(12) United States Patent
Streeter et al.

(10) Patent No.: US 7,309,348 B2
(45) Date of Patent: *Dec. 18, 2007

(54) METHOD FOR TREATMENT OF DEPRESSION

(75) Inventors: Jackson Streeter, Reno, NV (US); Luis De Taboada, Carlsbad, CA (US)

(73) Assignee: Photothera, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/038,770

(22) Filed: Jan. 19, 2005

(65) Prior Publication Data

US 2005/0187595 A1    Aug. 25, 2005

Related U.S. Application Data

(63) Continuation-in-part of application No. 10/764,986, filed on Jan. 26, 2004.

(60) Provisional application No. 60/537,190, filed on Jan. 19, 2004, provisional application No. 60/442,693, filed on Jan. 24, 2003.

(51) Int. Cl.
*A61N 5/06* (2006.01)

(52) U.S. Cl. ........................... 607/88; 128/898

(58) Field of Classification Search ................ 128/898; 607/88–94

See application file for complete search history.

(56) References Cited

U.S. PATENT DOCUMENTS

| | | |
|---|---|---|
| 3,735,755 A | 5/1973 | Eggleton et al. |
| 3,810,367 A | 5/1974 | Peterson |
| 4,315,514 A | 2/1982 | Drewes et al. |
| 4,343,301 A | 8/1982 | Indech |
| 4,630,273 A | 12/1986 | Inoue et al. |
| 4,633,872 A | 1/1987 | Chaffee et al. |
| 4,669,466 A | 6/1987 | L'Esperance |
| 4,798,215 A | 1/1989 | Turner |
| 4,846,196 A | 7/1989 | Wiksell et al. |

(Continued)

FOREIGN PATENT DOCUMENTS

EP    0 130 950    11/1990

(Continued)

OTHER PUBLICATIONS

U.S. Appl. No. 10/682,379, filed Oct. 9, 2003, De Taboada et al.

(Continued)

*Primary Examiner*—Henry M Johnson, III
(74) *Attorney, Agent, or Firm*—Knobbe Martens Olson & Bear LLP

(57) ABSTRACT

A method for treating or preventing depression is disclosed. The method, in preferred embodiments includes therapy apparatus for treating a patient's brain is provided. The method, in a preferred embodiment, includes irradiating at least a portion of a patient's brain with light energy having an efficacious power density and wavelength. The light energy should be sufficient to cause regulation of neurotransmitters in the brain and/or an upregulation of endogenous compounds in the brain, including neurotrophic factors, that result in neural growth, neurogenesis, and/or plasticity of neural function which leads to a diminishment or elimination of depression and its symptoms, and/or delays, reduces, or eliminates the onset of depression or depressive symptoms.

18 Claims, 17 Drawing Sheets

U.S. PATENT DOCUMENTS

| | | |
|---|---|---|
| 4,930,504 A | 6/1990 | Diamantopolous et al. |
| 4,951,482 A | 8/1990 | Gilbert |
| 4,951,653 A | 8/1990 | Fry et al. |
| 4,966,144 A | 10/1990 | Rochkind et al. |
| 5,029,581 A | 7/1991 | Kaga et al. |
| 5,037,374 A | 8/1991 | Carol |
| 5,054,470 A | 10/1991 | Fry et al. |
| 5,150,704 A | 9/1992 | Tatebayashi et al. |
| 5,259,380 A | 11/1993 | Mendes et al. |
| 5,267,294 A | 11/1993 | Kuroda et al. |
| 5,282,797 A | 2/1994 | Chess |
| 5,358,503 A | 10/1994 | Bertwell et al. |
| 5,401,270 A | 3/1995 | Muller et al. |
| 5,441,495 A | 8/1995 | Liboff et al. |
| 5,445,146 A * | 8/1995 | Bellinger .................... 607/89 |
| 5,445,608 A * | 8/1995 | Chen et al. .................. 604/20 |
| 5,464,436 A | 11/1995 | Smith |
| 5,474,528 A | 12/1995 | Meserol |
| 5,501,655 A | 3/1996 | Rolt et al. |
| 5,511,563 A | 4/1996 | Diamond |
| 5,540,737 A | 7/1996 | Fenn |
| 5,580,550 A | 12/1996 | Gough et al. |
| 5,580,555 A | 12/1996 | Schwartz |
| 5,601,526 A | 2/1997 | Chapelon et al. |
| 5,616,140 A | 4/1997 | Prescott |
| 5,621,091 A | 4/1997 | Kunkel et al. |
| 5,622,168 A | 4/1997 | Keusch et al. |
| 5,627,870 A | 5/1997 | Kopecky |
| 5,640,978 A | 6/1997 | Wong |
| 5,643,334 A | 7/1997 | Eckhouse et al. |
| 5,728,090 A | 3/1998 | Martin et al. |
| 5,755,752 A | 5/1998 | Segal |
| 5,817,008 A | 10/1998 | Rafert et al. |
| 5,842,477 A | 12/1998 | Naughton et al. |
| 5,843,073 A | 12/1998 | Sinofsky |
| 5,849,585 A | 12/1998 | Mather et al. |
| 5,879,376 A | 3/1999 | Miller |
| 5,902,741 A | 5/1999 | Purchio et al. |
| 5,928,207 A | 7/1999 | Pisano et al. |
| 5,928,945 A | 7/1999 | Seliktar et al. |
| 5,954,762 A | 9/1999 | Di Mino et al. |
| 5,983,141 A | 11/1999 | Sluijter et al. |
| 5,989,245 A | 11/1999 | Prescott |
| 6,030,767 A | 2/2000 | Wagner et al. |
| 6,033,431 A | 3/2000 | Segal |
| 6,042,531 A | 3/2000 | Holcomb |
| 6,045,575 A | 4/2000 | Rosen et al. |
| 6,046,046 A | 4/2000 | Hassanein |
| 6,060,306 A | 5/2000 | Flatt et al. |
| 6,063,108 A | 5/2000 | Salansky et al. |
| 6,100,290 A | 8/2000 | Levy et al. |
| 6,107,325 A | 8/2000 | Chan et al. |
| 6,107,608 A | 8/2000 | Hayes |
| 6,112,110 A | 8/2000 | Wilk |
| 6,117,128 A | 9/2000 | Gregory |
| 6,129,748 A | 10/2000 | Kamei |
| 6,143,878 A | 11/2000 | Koopman et al. |
| 6,146,410 A | 11/2000 | Nagypal et al. |
| 6,149,679 A | 11/2000 | Di Mino et al. |
| 6,156,028 A | 12/2000 | Prescott |
| 6,179,771 B1 | 1/2001 | Mueller |
| 6,187,210 B1 | 2/2001 | Lebouitz et al. |
| 6,198,958 B1 | 3/2001 | Ives et al. |
| 6,210,317 B1 | 4/2001 | Bonlie |
| 6,210,425 B1 | 4/2001 | Chen |
| 6,214,035 B1 | 4/2001 | Streeter |
| 6,221,095 B1 | 4/2001 | Van Zuylen et al. |
| 6,267,780 B1 | 7/2001 | Streeter |
| 6,273,905 B1 | 8/2001 | Streeter |
| 6,277,974 B1 | 8/2001 | Lo et al. |
| 6,290,713 B1 | 9/2001 | Russell |
| 6,290,714 B1 | 9/2001 | Streeter |
| 6,312,451 B1 | 11/2001 | Streeter |
| 6,344,050 B1 | 2/2002 | Chen |
| 6,358,272 B1 | 3/2002 | Wilden |
| 6,363,285 B1 | 3/2002 | Wey |
| 6,364,907 B1 | 4/2002 | Obochi et al. |
| 6,379,295 B1 | 4/2002 | Woo |
| 6,395,016 B1 | 5/2002 | Oron et al. |
| 6,397,107 B1 | 5/2002 | Lee et al. |
| 6,402,678 B1 | 6/2002 | Fischell et al. |
| 6,421,562 B1 | 7/2002 | Ross |
| 6,443,974 B1 | 9/2002 | Oron et al. |
| 6,443,978 B1 * | 9/2002 | Zharov .................... 607/91 |
| 6,471,716 B1 | 10/2002 | Pecukonis |
| 6,494,900 B1 | 12/2002 | Salansky et al. |
| 6,514,220 B2 | 2/2003 | Melton, Jr. et al. |
| 6,537,304 B1 * | 3/2003 | Oron ........................ 607/89 |
| 6,551,308 B1 | 4/2003 | Muller et al. |
| 6,602,274 B1 | 8/2003 | Chen |
| 6,663,659 B2 * | 12/2003 | McDaniel .................. 607/88 |
| 6,899,723 B2 | 5/2005 | Chen |
| 6,918,922 B2 * | 7/2005 | Oron ........................ 607/89 |
| 6,974,224 B2 * | 12/2005 | Thomas-Benedict ........ 362/103 |
| 2001/0044623 A1 | 11/2001 | Chen |
| 2002/0029071 A1 * | 3/2002 | Whitehurst ................ 607/88 |
| 2002/0068927 A1 | 6/2002 | Prescott |
| 2002/0087205 A1 | 7/2002 | Chen |
| 2002/0123781 A1 | 9/2002 | Shanks et al. |
| 2002/0188334 A1 | 12/2002 | Carlgren |
| 2002/0198575 A1 | 12/2002 | Sullivan |
| 2003/0125782 A1 | 7/2003 | Streeter |
| 2003/0144712 A1 | 7/2003 | Streeter |
| 2003/0167080 A1 * | 9/2003 | Hart et al. .................. 607/88 |
| 2003/0212442 A1 | 11/2003 | Streeter |
| 2003/0216797 A1 | 11/2003 | Oron |
| 2004/0014199 A1 | 1/2004 | Streeter |
| 2004/0015214 A1 * | 1/2004 | Simkin et al. ............... 607/88 |
| 2004/0044384 A1 | 3/2004 | Leber et al. |
| 2004/0073278 A1 | 4/2004 | Pachys |
| 2004/0132002 A1 | 7/2004 | Streeter |
| 2004/0138727 A1 * | 7/2004 | Taboada et al. ............. 607/88 |
| 2004/0220513 A1 | 11/2004 | Streeter |
| 2004/0260367 A1 | 12/2004 | De Taboada et al. |
| 2005/0009161 A1 | 1/2005 | Streeter |
| 2005/0107851 A1 | 5/2005 | De Taboada et al. |
| 2005/0203595 A1 * | 9/2005 | Oron ........................ 607/89 |

FOREIGN PATENT DOCUMENTS

| | | |
|---|---|---|
| EP | 0 763 371 A2 | 3/1997 |
| EP | 0 783 904 A2 | 7/1997 |
| EP | 1 226 787 A2 | 7/2002 |
| JP | 04023634 | 2/1992 |
| WO | WO96/36396 | 11/1996 |
| WO | WO98/04321 | 2/1998 |
| WO | WO98/22573 | 5/1998 |
| WO | WO99/42178 | 8/1999 |
| WO | WO99/62599 A1 | 12/1999 |
| WO | WO 00/035534 A1 | 6/2000 |
| WO | WO 2005/025672 A1 | 3/2005 |

OTHER PUBLICATIONS

U.S. Appl. No. 10/448,262, filed May 29, 2003, Oron et al.
U.S. Appl. No. 10/612,709, filed Jul. 2, 2003, Streeter.
U.S. Appl. No. 10/723,171, filed Nov. 26, 2003, Streeter.
U.S. Appl. No. 10/764,986, filed Jan. 6, 2004, Streeter.
PCT/US03/00747 International Search Report.
PCT/US02/36808 International Search Report.
PCT/CA99/00156 International Search Report.
PCT/US04/029724 International Search Report.
PCT/US2005/004873 Partial ISR dated Jun. 16, 2005, Photothera, Inc.

*Optical Properties of Tissues with Strong (Multiple) Scattering*, source unknown.

Agov, B.S., et al., *On the mechanism of therapeutic action of helium-neon laser in ischemic heart disease*, Klin Med (Mosc), 1985, pp. 102-105 (Abstract Only).

Alton, et al., *Gene Therapy: The Case for Cystic Fibrosis*, J.R. Soc. Med 90 Suppl 31: 43-46 1997.

Anderson, *Human Gene Therapy*, Nature 392: 25-30, Apr. 1998.

Arvidsson, Andreas, et al., *Neuronal replacement from endogenous precursors in the adult rat brain after stroke*, Nature Medicine, vol. 8, No. 9, Sep. 2002, pp. 963-970.

Boucher, *Current Status of Gene Therapy*, TIG 12(3):81-84, Mar. 1996.

Boucher, *Status of Gene Therapy for Cystic Fibrosis Lung Disease*, J. Clin. Invest. 103(4): 441-455 Feb. 1999.

Brazzle, John, et al., *Active Microneedles with Integrated Functionality*, Technical Digest of the 2000 Solid-State Sensor and Actuator Workshop, Department of Bioengineering, University of Utah, Salt Lake City, Utah 84112 (five pages).

Brill, G.E., et al., *Modifying influence of low level laser irradiation on the relationships in endothelial cell—blood platelet system*, 10th Congress of the European Society for Photobiology, Vienna, Austria (one page).

Cohen, Michael A., *Method of Forming Microneedles and other Micron-Scale Transdermal Probes*, Office of Technology Licensing, University of California, Berkeley, http://ot1.berkeley.edu/technology/inventiondetail.php/1000335, Abstract (two pages).

Davies, et al., *Prospects for Gene Therapy for Cystic Fibrosis*, Mol. Med Today 4(7): 292-299, Jul. 1998, pp. 294, col. 2, lines 20-28.

Dirnagl, Ulrich, et al., *Pathobiology of ischaemic stroke: an integrated view*, TINS, vol. 22, No. 9, 1999, pp. 391-397.

Eells, J.T., et al., *Therapeutic photobiomodulation for methanol-induced retinal toxicity*, Proceedings National Academy of Science (PNAS), vol. 100, No. 6, Mar. 18, 2003, pp. 3439-3444.

Elimadi, Aziz, et al., *Trimetazidine Counteracts the Hepatic Injury Associated with Ischemia-Reperfusion by Preserving Michondrial Function*, Journal of Pharmacology and Experimental Therapeutics, vol. 286, No. 1, 1998, pp. 23-28.

Ferrari, et al., *Barriers to and New Approaches for Gene Therapy and Gene Delivery in Cystic Fibrosis*, Adv. Drug Del. Rev 54: 1373-1393, 2002.

Gage, Fred H., *Brain, Repair Yourself*, Scientific American, Sep. 2003, pp. 47-53.

Gasparyan, Levon V., et al., *Low Level Laser Therapy of Male Genital Tract Chronic Inflammations*, WALT 2-nd Congress (Kansas City, USA), 1998 (two pages).

Gasparyan, L. V., et al., *The influence of LED irradiation at different wavelengths on functional activity of blood platelets*, 10th Congress of the European Society for Photobiology, Vienna, Austria 2003 (one page).

Gasparyan, Levon V., *Biochemical and Biophysical Effects of Low Level Laser Irradiation*, MAL 2000, Helsinki, Finland (three pages).

Gasparyan, Levon V., *Experience of Russian ( former USSR) Scientists in LLLT and UV Blood Irradiation*, MAL 2000, Helsinki, Finland (four pages).

Gasparyan, Levon V., *Investigation of Sensations, Associated with Laser Blood Irradiation*, WALT 2-nd Congress (Kansas City, USA), 1998 (two pages).

Gasparyan, Levon V., *Millimeter Wave Therapy*, MAL 2000, Helsinki, Finland (three pages).

Gross, Garrett J., et al., *Mechanisms of Postischemic Contractile Dysfunction*, Myocardial Protection From Surgical Ischemic-Reperfusion Injury, An International Symposium, Asheville, North Carolina, Sep. 21-24, 1997, pp. 1898-1904.

Hammon, John W. Jr, MD, et al., *Myocardial Protection From Surgical Ischemic-Reperfusion Injury*, Ann Thorac Surg 1999:68:1897.

Iadecola, Costantino, et al., *Inhibition of inducible nitric oxide synthase ameliorates ischemic damage*, Am. J. Physiol., vol. 268, 1995, pp. R286-R292.

Karu, Tiina, *Mechanisms of Low-Power Laser Light Action on Cellular Level*, Effects of Low-Power Light on Biological Systems V, Proceedings of SPIE, Jul. 7, 2000, vol. 4159, 2000.

Karu, T.I., *Low power laser therapy*, in Biomedical Photonics Handbook, Ch. 48, Editor-in-Chief Tuan Vo-Dinh, Boca Raton, CRC Press, 2003.

Karu, Tiina, *Mechanisms of interaction of monochromatic visible light with cells*, Proc. SPIE, vol. 2630, pp. 2-9.

Karu, Tiina, *Photobiological Fundamentals of Low Power Laser Therapy*, IEEE Journal of Quantum Electronics, vol. QE-23, No. 10, Oct. 1987, pp. 1703-1717.

*The Laser Exchange: Delivering the medicine of the future*, www.laserexchange.co.uk/laser-therapy/ultrasoun.htm, 42 pages.

Leung, Mason C.P., et al., *Treatment of Experimentally Induced Transient Cerebral Ischemia with Low Energy Laser Inhibits Nitric Oxide Synthase Activity and Up-Regulates the Expression of Transforming Growth Factor-Beta 1*, Lasers in Surgery and Medicine, vol. 31, 2002, pp. 283-288.

Minoru, Asahi, et al, *Expression of Interleukin-1 [beta] Converting Enzyme Geme Family and bcl-2 Gene Family in the Rat Brain Following Permanent Occlusion of the Middle Cerebral Artery*, Journal of Cerebral Blood Flow & Metabolism, vol. 17(1), Jan. 1997, pp. 11-18.

Mochizuki-Oda, Noriko, et al., *Effects of near-infra-red laser irradiation on adenosine triphosphate and adenosine diphosphate contents of rat brain tissue*, Neuroscience Letters 323, May 3, 2002, pp. 207-210.

Nishioka, Norman S., et al., *Reflection and Transmission of Laser Light From the Esophagus: The Influence of Incident Angle*, Gastroenterology, vol. 94, 1988, pp. 1180-1185.

Olesin, Al, et al., *Laser irradiation of venous blood for production of reperfusion syndrome in myocardial infarction*, Patologisheskaia fiziologiia, 1992 (Abstract Only).

Oron , Uri, et al., *Attenuation of Infarct Size in Rats and Dogs after Myocardial Infarction by Low-Energy Laser Irradiation*, Lasers in Surgery and Medicine, vol. 28, 2001, pp. 204-211.

Oron, Uri, et al., *Low-Energy Laser Irradiation Reduces Formation of Scar Tissue After Myocardial Infarction in Rats and Dogs*, Circulation, vol. 103, Jan. 16, 2001, pp. 296-301.

Park, James L., Ph.D., et al., *Mechanisms of Myocardial Reperfusion Injury*, The Annals of Thoracic Surgery, Official Journal of The Society of Thoracic Surgeons and the Southern Thoracic Surgical Association, vol. 68, No. 5, Nov. 1999, pp. 1905-1912.

Romano, et al., *Latest Developments in Gene Transfer Technology: Achievements, Perspectives, and Controversies over Therapeutic Applications*, Stem Cells 18: 19-39, 2000.

Rosenecker, et al., *Towards Gene Therapy of Cystic Fibrosis*, Eur. J. Med. 23(3): 149-156, Mar. 1998.

Rosenfeld, et al., *Impact of Basic Research on Tomorrow's Medicine*, Chest 109: 241-252, 1996).

Semenza, Gregg L., et al., *Regulation of Mammalian $O_2$ Homeostasis by Hypoxia-Inducible Factor I*, Ann. Rev. Cell Dev. Biol., vol. 15, 1999, pp. 551-578.

Somia, et al., *Gene Therapy: Trials and Tribulations*, Nature Reviews Genetics 1: 91-99, 2000.

Stys, Peter K., *Anoxis and Ischemic Injury of Myelinated Axons in CNS White Matter: From Mechanistic Concepts to Therapeutics*, J. Cereb. Blood Flow Metab., vol. 18, No. 1, Jan. 1998, pp. 2-25.

*Is LLLT Different from Ultrasound?*, http://www.thorlaser.com/LLLT/is-LLLT-diff-from-ultrasound.htm, 2 pages.

Product List, Tho, lllt, LLLT, *Low Level Laser Therapy, Laz.*, http://www.thorlaser.com/prodlist/index.html, Oct. 6, 1999, pp. 1-4.

Specifications, Thor, lllt, LLLT, *Low Level Laser Therapy, low level laser therapy*, http://www.thorlaser.com/specs, Oct. 6, 1999, pp. 1-2.

100mW, Thor, lllt, LLLT, *Low Level Laser Therapy, low level laser therapy, Lazer, ThorI.*, http://www.thorlaser.com/ specs/ 100m W.html, Oct. 6, 1999, p. 1.

200mW, Thor, lllt, LLLT, *Low Level Laser Therapy, low level laser therapy, Lazer, ThorI.*, http://www.thorlaser.com/ specs/200m W.html, Oct. 6, 1999, p. 1.

500mW, Thor, lllt, LLLT, *Low Level Laser Therapy, low level laser therapy, Lazer, Thorl.*, http://www.thorlaser.com/ specs/500mW.html, Oct. 6, 1999, p. 1.

200mW, Thor, lllt, LLLT, *Low Level Laser Therapy, low level laser therapy, Laser, Thorl.*, http://www.thorlaser.com/ specs/200mW650nm.html, Oct. 6, 1999, p. 1.

680nm Probe, Thor, lllt, LLLT, *Low Level Laser Therapy, low level laser therapy, Laser*, http://www.thorlaser.com/ specs/680.html, Oct. 6, 1999, p. 1.

Toon, John, *Taking the "Ouch" Out of Needles: Arrays of Micron-Scale "Microneedles" Offer New Technique for Drug Delivery, Georgia Tech Research News*, Jun. 22, 1998 (three pages).

Toricelli, P., et al., *Laser Biostimulation of cartilage: in vitro evaluation, Biomed Pharmacother* 2001, vol. 55, pp. 117-120.

Tuchin, Valery, *Tissue Optics: Light Scattering Methods and Instruments for Medical Diagnosis*, SPIE Press, Tutorial Texts in Optical Engineering, vol. TT38, 2000, pp. 3-11.

Van Brugel, Hans H.F.I., et al., *Power Density and Exposure Time of He-Ne Laster Irradation ar eMore Important than Total Energy Dose in Photo-Biomoducation of Human Fibroblasts* In Vitro, 1992, Wiley-Liss, Inc.

Verma, et al., *Gene Therapy—promises, problems and prospects*, Nature 389:239-242, 1997.

Wilson, *Gene Therapy for Cystic Fibrosis: Challenges and Future Directions*, J. Clin. Invest 96: 2547-2554, Dec. 1995.

Wong-Riley, Margaret T.T., et al., *Light-emitting diode treatment reverses the effect of TTX on cytochrome oxidase in neurons, NeuroReport*, vol. 12, No. 14, Oct. 8, 2001, pp. 3033-3037.

Yaakobi, Tali, et al., *Long-term effect of low energy laser irradiation on infarction and reperfusion injury in the rate heart, J. Appl. Physiol.*, vol. 90, 2001, pp. 2411-2419.

\* cited by examiner

METHOD FOR TREATMENT OF DEPRESSION

RELATED APPLICATION INFORMATION

This application claims priority under 35 U.S.C. § 119 (e) to U.S. Provisional Application Ser. No. 60/537,190 filed Jan. 19, 2004 and is a Continuation In Part of U.S. application Ser. No. 10/764,986 filed Jan. 26, 2004, which claims priority under 35 U.S.C. § 119 (e) to U.S. Provisional Application Ser. No. 60/442,693 filed Jan. 24, 2003, the disclosures of which are hereby incorporated by reference in their entireties.

BACKGROUND OF THE INVENTION

1. Field of the Invention

The present invention relates in general to treatment of depression and depressive symptoms, and more particularly, to of treatment using phototherapy of brain tissue.

2. Description of the Related Art

In the U.S., it is believed that approximately 10% of people suffer from depression at any one time, and 20%-25% suffer an episode of depression at some point during their lifetimes. The disease affects people of all ages, including children, adults, and the elderly, and disproportionally affects women, with about twice as many women as men suffering from depression at some point in their lives. Additionally, persons who suffer one episode of major depression are much more likely to have additional episodes than those who have not experienced serious depression.

There are several types of depression which vary in severity and average episode length. Two of the most common types are major depression and chronic depression or Dysthmia. Chronic depression is generally a less severe form of depression, having milder but longer lasting symptoms than major depression. The symptoms of both types of depression are essentially the same, and include sadness, loss of energy, feelings of hopelessness, difficulty concentrating, insomnia, and irritability. Individuals suffering depression are also more likely to engage in drug or alcohol abuse, and if untreated, depression can lead to violence, including suicide.

All types of depression, including major and chronic depression, are commonly treated by one or both of antidepressant medication and psychotherapy. Other forms of treatment, such as electroconvulsive therapy (ECT) are also used, albeit less frequently. There are several types of antidepressant medications presently available, including tricyclic antidepressants (TCAs), monoamine oxidase inhibitors (MAOIs), selective serotonin reuptake inhibitors (SSRIs), and selective norepinephrine reuptake inhibitors (SSNRIs). Although the widely prescribed SSRIs cause fewer severe side effects than the older TCA and MAOI drugs, they are not without their own unpleasant effects, including dizziness, insomnia, and reduced sexual desire and performance. Despite their widespread use, antidepressant medications are only moderately successful, helping only about 70% of the people who take them.

Against this background, a high level of interest remains in finding new and improved methods for the treatment of depression that exhibit higher rates of effectiveness and fewer side effects of available drug therapy.

SUMMARY OF THE INVENTION

In accordance with one embodiment, there is provided a method for treating depression comprising irradiating at least a portion of a patient's brain with light energy having an efficacious power density and wavelength. The light energy is sufficient to cause a diminishment or elimination of depression and its symptoms, and/or delays, reduces, or eliminates the onset of depression or depressive symptoms. It is believed that the radiation causes an upregulation of endogenous compounds in the brain, including neurotrophic factors, that serve to enhance neural growth, neurogenesis, and/or plasticity of neural function that cause the beneficial effects in the brain, and/or that the radiation results in a more normal balance of neurotransmitters in the brain.

Other embodiments also each provide a method for treating, preventing, or reducing the symptoms of depression. Such methods preferably result in the upregulation of endogenous compounds useful in treating depression, reducing the symptoms or severity of depression, or preventing depression, including neurotrophic factors that cause or promote neurogenesis, neural growth, and/or plasticity of neural function. One such method comprises introducing light of an efficacious power density onto brain tissue by directing light through the scalp of a patient. Directing the light comprises providing a sufficiently large spot size on said scalp to reduce the power density at the scalp below the damage threshold of scalp tissue, while producing sufficient optical power at the scalp to achieve said efficacious power density at the brain tissue. Another such method comprises directing an efficacious power density of light through the scalp of the patient to a target area of the brain and/or to the cortex of the brain concurrently with applying an efficacious amount of ultrasonic energy or an electromagnetic field to the brain. Yet another method comprises introducing light of an efficacious power density onto a target area of the brain and/or to the cortex of the brain by directing light through the scalp of the patient. The light has a plurality of wavelengths and the efficacious power density is at least 0.01 mW/cm$^2$ at the target area.

In preferred embodiments, the methods utilize a therapy apparatus for treating a patient's brain. One suitable therapy apparatus comprises a light source having an output emission area positioned to irradiate a portion of the brain with an efficacious power density and wavelength of light. The therapy apparatus further comprises an element interposed between the light source and the patient's scalp. The element is adapted to inhibit temperature increases at the scalp caused by the light.

Another suitable therapy apparatus comprises a light source positioned to irradiate at least a portion of a patient's head with light. The light has a wavelength and power density which penetrates the cranium to deliver an efficacious amount of light to brain tissue. The therapy apparatus further comprises a material which inhibits temperature increases of the head.

Another suitable therapy apparatus comprises a light source adapted to irradiate at least a portion of the brain with an efficacious power density and wavelength of light. The therapy apparatus further comprises an element adapted to inhibit temperature increases at the scalp. At least a portion of the element is in an optical path of the light from the light source to the scalp.

Another suitable therapy apparatus comprises a light source adapted to irradiate at least a portion of the brain with an efficacious power density and wavelength of light. The therapy apparatus further comprises a controller for energizing said light source so as to selectively produce a plurality of different irradiation patterns on the patient's scalp. Each of said irradiation patterns is comprised of at least one illumination area that is small compared to the patient's scalp, and at least one non-illuminated area.

Another suitable therapy apparatus comprises a light source adapted to irradiate at least a portion of the brain with an efficacious power density and wavelength of light. The therapy apparatus further comprises a biomedical sensor configured to provide real-time feedback information. The therapy apparatus further comprises a controller coupled to the light source and the biomedical sensor. The controller is configured to adjust said light source in response to the real-time feedback information.

For purposes of summarizing the present invention, certain aspects, advantages, and novel features of the present invention have been described herein above. It is to be understood, however, that not necessarily all such advantages may be achieved in accordance with any particular embodiment of the present invention. Thus, the present invention may be embodied or carried out in a manner that achieves or optimizes one advantage or group of advantages as taught herein without necessarily achieving other advantages as may be taught or suggested herein.

DETAILED DESCRIPTION OF THE PREFERRED EMBODIMENT

Figure 1:
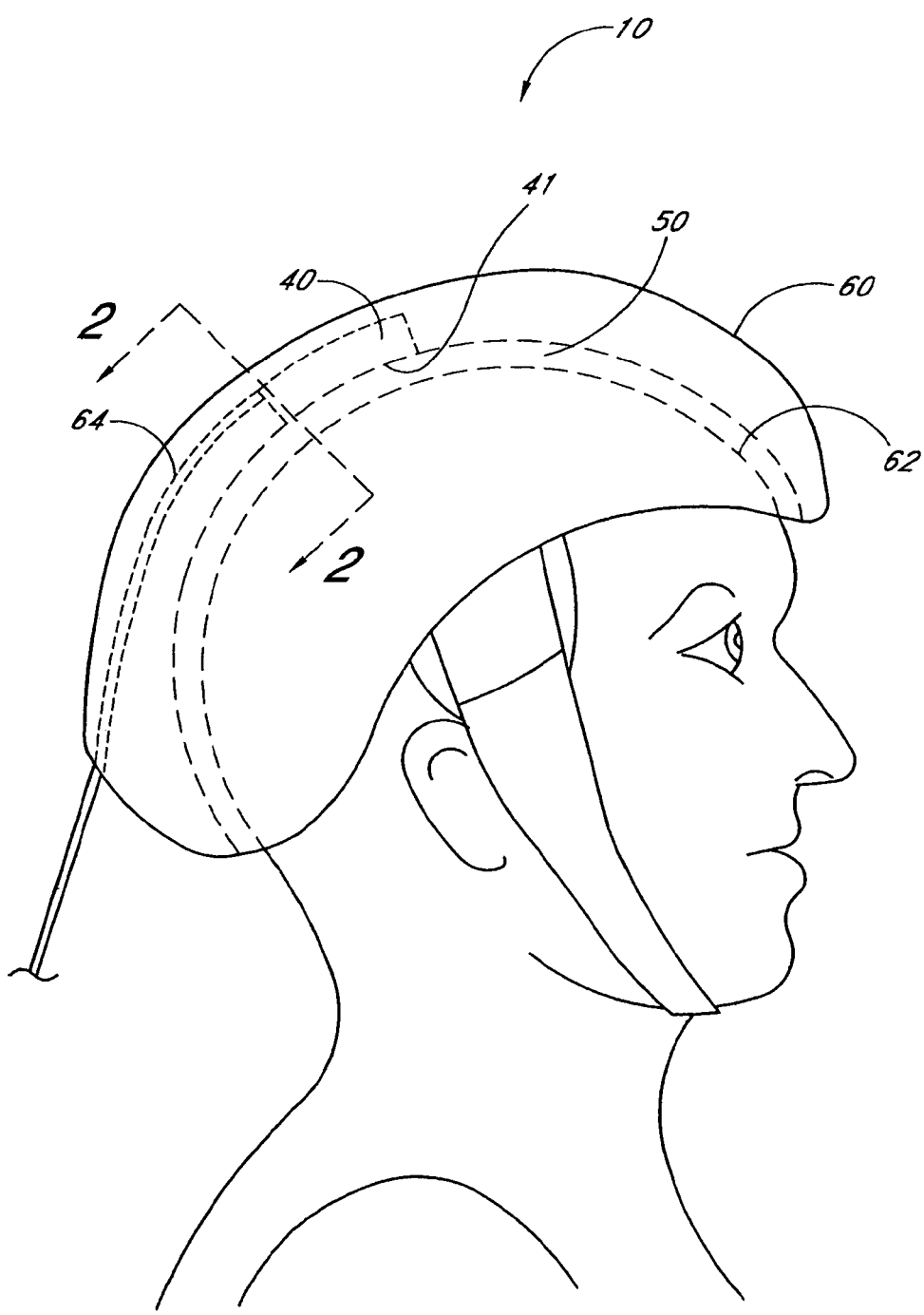
FIG. 1 schematically illustrates a therapy apparatus comprising a cap which fits securely over the patient's head.

It has recently been proposed that depression is caused by the action of stress hormones. Stress hormones such as corticotrophin-releasing hormone (CRH) result in a decrease in compounds called neurotrophic factors that are responsible for neurogenesis and neural growth, including the growth of neural projections such as dendrites and axons, as well as a decrease in the flexibility of synapses.

Accordingly, therapy that results in the upregulation of neurotrophic factors and other endogenous compounds that cause or assist neurogenesis and neural growth should be useful in treating depression, reducing the symptoms or severity of depression, or preventing depression. Therapy that causes the regulation of neurotransmitters in the brain such that their concentrations are at more normal levels, much like the various pharmacological therapies, should also be useful against depression. Low level light therapy ("LLLT") or phototherapy administered to the brain is believed to achieve these desired effects.

Low level light therapy or phototherapy involves therapeutic administration of light energy to a patient at lower power outputs than those used for cutting, cauterizing, or ablating biological tissue, resulting in desirable biostimulatory effects while leaving tissue undamaged. In non-invasive phototherapy, it is desirable to apply an efficacious amount of light energy to the internal tissue to be treated using light sources positioned outside the body. (See, e.g., U.S. Pat. No. 6,537,304 to Oron and U.S. patent application Ser. Nos. 10/353,130, 10/682,379 filed Oct. 9, 2003, and Ser. No. 10/938,423 filed Sep. 10, 2004, all of which are hereby incorporated by reference in their entireties. However, absorption of the light energy by intervening tissue can limit the amount of light energy delivered to the target tissue site, while heating the intervening tissue. In addition, scattering of the light energy by intervening tissue can limit the power density or energy density delivered to the target tissue site. Brute force attempts to circumvent these effects by increasing the power and/or power density applied to the outside surface of the body can result in damage (e.g., burning) of the intervening tissue.

Non-invasive phototherapy methods are circumscribed by setting selected treatment parameters within specified limits so as to preferably avoid damaging the intervening tissue. A review of the existing scientific literature in this field would cast doubt on whether a set of undamaging, yet efficacious, parameters could be found. However, certain embodiments, as described herein, provide devices and methods which can achieve this goal.

Such embodiments may include selecting a wavelength of light at which the absorption by intervening tissue is below a damaging level. Such embodiments may also include setting the power output of the light source at very low, yet efficacious, power densities (e.g., between approximately 100 µW/cm² to approximately 10 W/cm²) at the target tissue site, and time periods of application of the light energy at a few seconds to minutes to achieve an efficacious energy density at the target tissue site being treated, such target tissue being on the cortex or being within the brain. Other parameters can also be varied in the use of phototherapy. These other parameters contribute to the light energy that is actually delivered to the treated tissue and may play key roles in the efficacy of phototherapy. In certain embodiments, the irradiated portion of the brain can comprise the entire brain.

Element to Inhibit Temperature Increases at the Scalp

Figure 2:
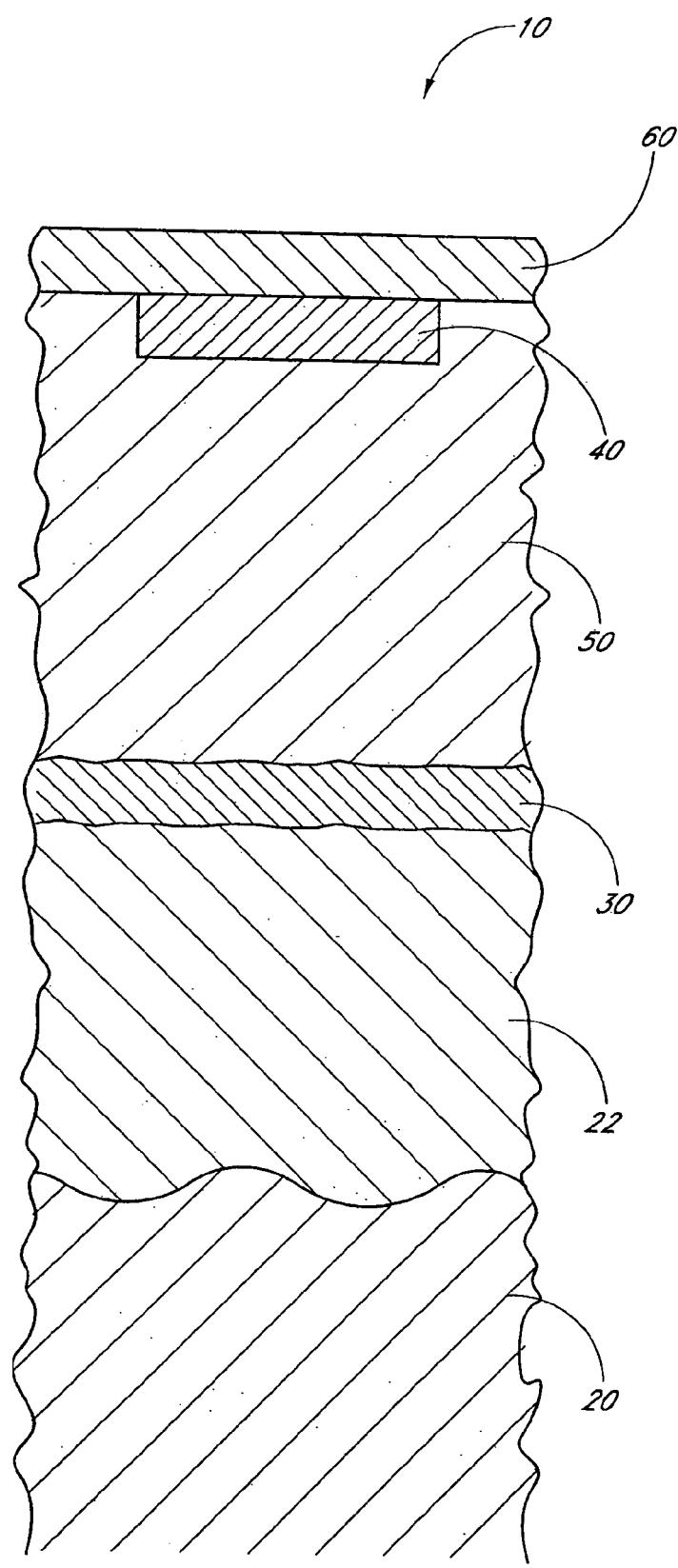
FIG. 2 schematically illustrates a fragmentary cross-sectional view taken along the lines 2-2 of FIG. 1, showing one embodiment of a portion of a therapy apparatus comprising an element and its relationship to the scalp and brain.

FIGS. 1 and 2 schematically illustrate an embodiment of a therapy apparatus 10 for treating a patient's brain 20. The therapy apparatus 10 comprises a light source 40 having an output emission area 41 positioned to irradiate a portion of the brain 20 with an efficacious power density and wavelength of light. The therapy apparatus 10 further comprises an element 50 interposed between the light source 40 and the patient's scalp 30. The element 50 is adapted to inhibit temperature increases at the scalp 30 caused by the light.

As used herein, the term "element" is used in its broadest sense, including, but not limited to, as a reference to a constituent or distinct part of a composite device. In certain embodiments, the element 50 is adapted to contact at least a portion of the patient's scalp 30, as schematically illustrated in FIGS. 1-4. In certain such embodiments, the element 50 is in thermal communication with and covers at least a portion of the scalp 30. In other embodiments, the element 50 is spaced away from the scalp 30 and does not contact the scalp 30.

In certain embodiments, the light passes through the element 50 prior to reaching the scalp 30 such that the element 50 is in the optical path of light propagating from the light source 40, through the scalp 30, through the bones, tissues, and fluids of the head (schematically illustrated in FIG. 1 by the region 22), to the brain 20. In certain embodiments, the light passes through a transmissive medium of the element 50, while in other embodiments, the light passes through an aperture of the element 50. As described more fully below, the element 50 may be utilized with various embodiments of the therapy apparatus 10.

In certain embodiments, the light source 40 is disposed on the interior surface of a cap 60 which fits securely over the patient's head. The cap 60 provides structural integrity for the therapy apparatus 10 and holds the light source 40 and element 50 in place. Exemplary materials for the cap 60 include, but are not limited to, metal, plastic, or other materials with appropriate structural integrity. The cap 60 may include an inner lining 62 comprising a stretchable fabric or mesh material, such as Lycra or nylon. In certain embodiments, the light source 40 is adapted to be removably attached to the cap 60 in a plurality of positions so that the output emission area 41 of the light source 40 can be advantageously placed in a selected position for treatment of any portion of the brain 20. In other embodiments, the light source 40 can be an integral portion of the cap 60.

The light source 40 illustrated by FIGS. 1 and 2 comprises at least one power conduit 64 coupled to a power source (not shown). In some embodiments, the power conduit 64 comprises an electrical conduit which is adapted to transmit electrical signals and power to an emitter (e.g., laser diode or light-emitting diode). In certain embodiments, the power conduit 64 comprises an optical conduit (e.g., optical waveguide) which transmits optical signals and power to the output emission area 41 of the light source 40. In certain such embodiments, the light source 40 comprises optical elements (e.g., lenses, diffusers, and/or waveguides) which transmit at least a portion of the optical power received via the optical conduit 64. In still other embodiments, the therapy apparatus 10 contains a power source (e.g., a battery) and the power conduit 64 is substantially internal to the therapy apparatus 10.

In certain embodiments, the patient's scalp 30 comprises hair and skin which cover the patient's skull. In other embodiments, at least a portion of the hair is removed prior to the phototherapy treatment, so that the therapy apparatus 10 substantially contacts the skin of the scalp 30.

In certain embodiments, the element 50 is adapted to contact the patient's scalp 30, thereby providing an interface between the therapy apparatus 10 and the patient's scalp 30. In certain such embodiments, the element 50 is coupled to the light source 40 and in other such embodiments, the element is also adapted to conform to the scalp 30, as schematically illustrated in FIG. 1. In this way, the element 50 positions the output emission area 41 of the light source 40 relative to the scalp 30. In certain such embodiments, the element 50 is mechanically adjustable so as to adjust the position of the light source 40 relative to the scalp 30. By fitting to the scalp 30 and holding the light source 40 in place, the element 50 inhibits temperature increases at the scalp 30 that would otherwise result from misplacement of the light source 40 relative to the scalp 30. In addition, in certain embodiments, the element 50 is mechanically adjustable so as to fit the therapy apparatus 10 to the patient's scalp 30.

In certain embodiments, the element 50 provides a reusable interface between the therapy apparatus 10 and the patient's scalp 30. In such embodiments, the element 50 can be cleaned or sterilized between uses of the therapy apparatus, particularly between uses by different patients. In other embodiments, the element 50 provides a disposable and replaceable interface between the therapy apparatus 10 and the patient's scalp 30. By using pre-sterilized and pre-packaged replaceable interfaces, certain embodiments can advantageously provide sterilized interfaces without undergoing cleaning or sterilization processing immediately before use.

In certain embodiments, the element 50 comprises a container (e.g., a cavity or bag) containing a material (e.g., gel). The container can be flexible and adapted to conform to the contours of the scalp 30. Other exemplary materials contained in the container of the element 50 include, but are not limited to, thermal exchange materials such as glycerol and water. The element 50 of certain embodiments substantially covers the entire scalp 30 of the patient, as schematically illustrated in FIG. 2. In other embodiments, the element 50 only covers a localized portion of the scalp 30 in proximity to the irradiated portion of the scalp 30.

In certain embodiments, at least a portion of the element 50 is within an optical path of the light from the light source 40 to the scalp 30. In such embodiments, the element 50 is substantially optically transmissive at a wavelength of the light emitted by the output emission area 41 of the light source 40 and is adapted to reduce back reflections of the light. By reducing back reflections, the element 50 increases the amount of light transmitted to the brain 20 and reduces the need to use a higher power light source 40 which may otherwise create temperature increases at the scalp 30. In certain such embodiments, the element 50 comprises one or more optical coatings, films, layers, membranes, etc. in the optical path of the transmitted light which are adapted to reduce back reflections.

In certain such embodiments, the element 50 reduces back reflections by fitting to the scalp 30 so as to substantially reduce air gaps between the scalp 30 and the element 50 in the optical path of the light. The refractive-index mismatches between such an air gap and the element 50 and/or the scalp 30 would otherwise result in at least a portion of the light propagating from the light source 40 to the brain 20 to be reflected back towards the light source 40.

In addition, certain embodiments of the element 50 comprise a material having, at a wavelength of light emitted by the light source 40, a refractive index which substantially matches the refractive index of the scalp 30 (e.g., about 1.3), thereby reducing any index-mismatch-generated back reflections between the element 50 and the scalp 30. Examples of materials with refractive indices compatible with embodiments described herein include, but are not limited to, glycerol, water, and silica gels. Exemplary index-matching gels include, but are not limited to, those available from Nye Lubricants, Inc. of Fairhaven, Mass.

In certain embodiments, the element 50 is adapted to cool the scalp 30 by removing heat from the scalp 30 so as to inhibit temperature increases at the scalp 30. In certain such embodiments, the element 50 comprises a reservoir (e.g., a chamber or a conduit) adapted to contain a coolant. The coolant flows through the reservoir near the scalp 30. The scalp 30 heats the coolant, which flows away from the scalp 30, thereby removing heat from the scalp 30 by active cooling. The coolant in certain embodiments circulates between the element 50 and a heat transfer device, such as a chiller, whereby the coolant is heated by the scalp 30 and is cooled by the heat transfer device. Exemplary materials for the coolant include, but are not limited to, water or air.

Figure 3:
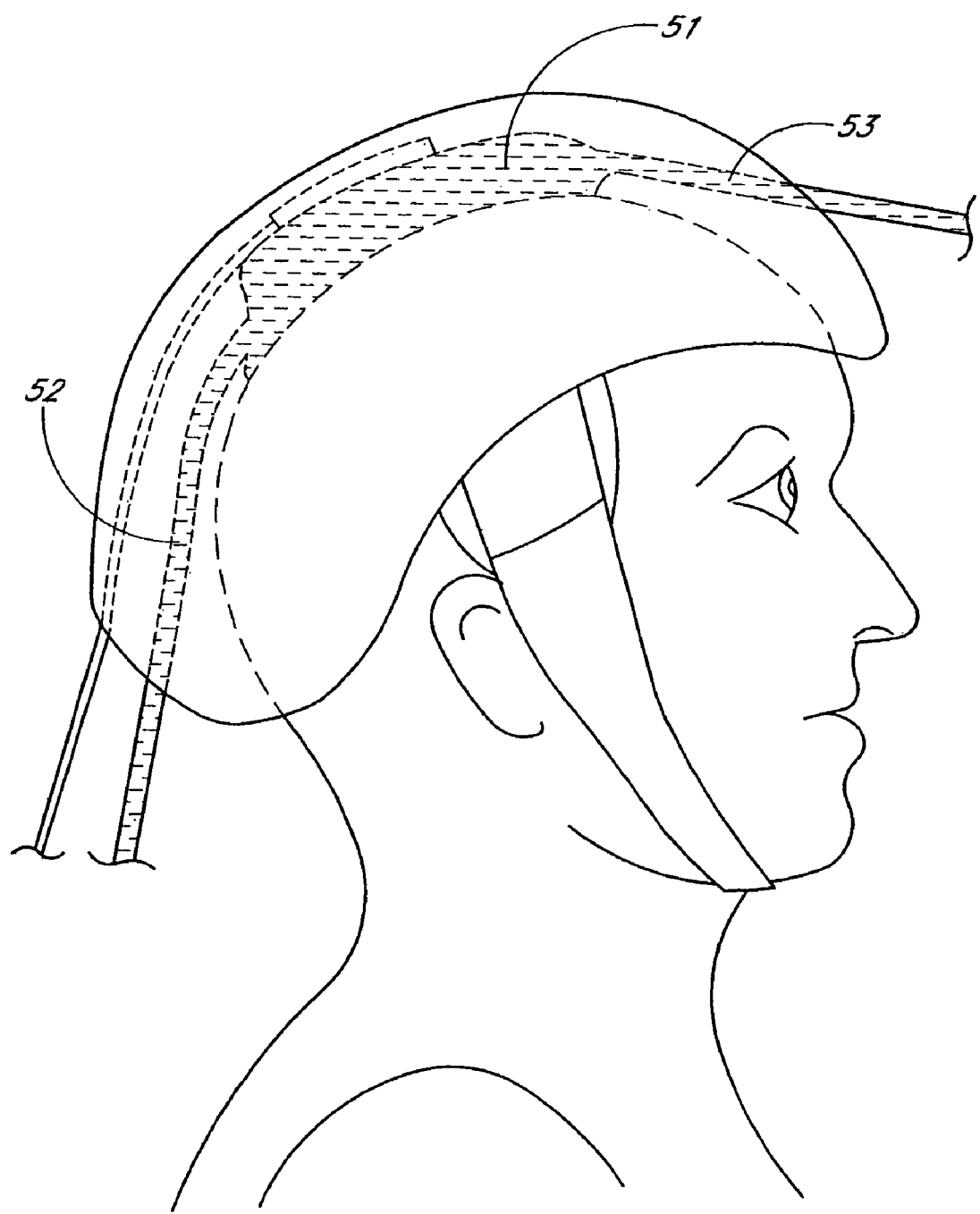
FIG. 3 schematically illustrates an embodiment with an element comprising a container coupled to an inlet conduit and an outlet conduit for the transport of a flowing material through the element.

In certain embodiments, the element 50 comprises a container 51 (e.g., a flexible bag) coupled to an inlet conduit 52 and an outlet conduit 53, as schematically illustrated in FIG. 3. A flowing material (e.g., water, air, or glycerol) can flow into the container 51 from the inlet conduit 52, absorb heat from the scalp 30, and flow out of the container 51 through the outlet conduit 53. Certain such embodiments can provide a mechanical fit of the container 51 to the scalp 30 and sufficient thermal coupling to prevent excessive heating of the scalp 30 by the light. In certain embodiments, the container 51 can be disposable and replacement containers 51 can be used for subsequent patients.

In still other embodiments, the element 50 comprises a container (e.g., a flexible bag) containing a material which does not flow out of the container but is thermally coupled to the scalp 30 so as to remove heat from the scalp 30 by passive cooling. Exemplary materials include, but are not limited to, water, glycerol, and gel. In certain such embodiments, the non-flowing material can be pre-cooled (e.g., by placement in a refrigerator) prior to the phototherapy treatment to facilitate cooling of the scalp 30.

In certain embodiments, the element 50 is adapted to apply pressure to at least a portion of the scalp 30. By applying sufficient pressure, the element 50 can blanch the portion of the scalp 30 by forcing at least some blood out the optical path of the light energy. The blood removal resulting from the pressure applied by the element 50 to the scalp 30 decreases the corresponding absorption of the light energy by blood in the scalp 30. As a result, temperature increases due to absorption of the light energy by blood at the scalp 30 are reduced. As a further result, the fraction of the light energy transmitted to the subdermal target tissue of the brain 20 is increased.

Figure 4A:
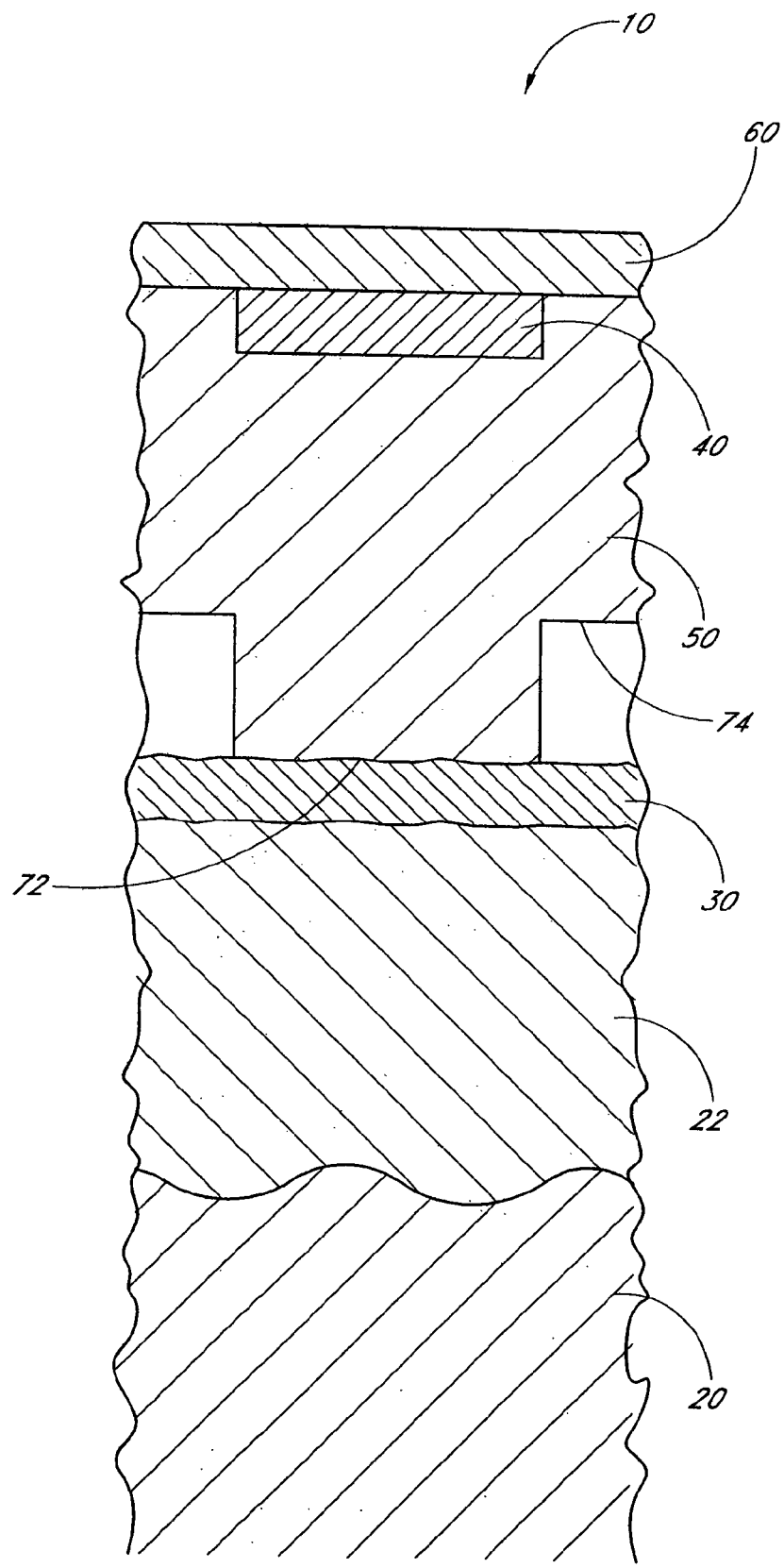
FIG. 4A schematically illustrates a fragmentary cross-sectional view taken along the lines 2-2 of FIG. 1, showing another embodiment of a portion of a therapy apparatus comprising an element with a portion contacting the scalp and a portion spaced away from the scalp.
Figure 4B:
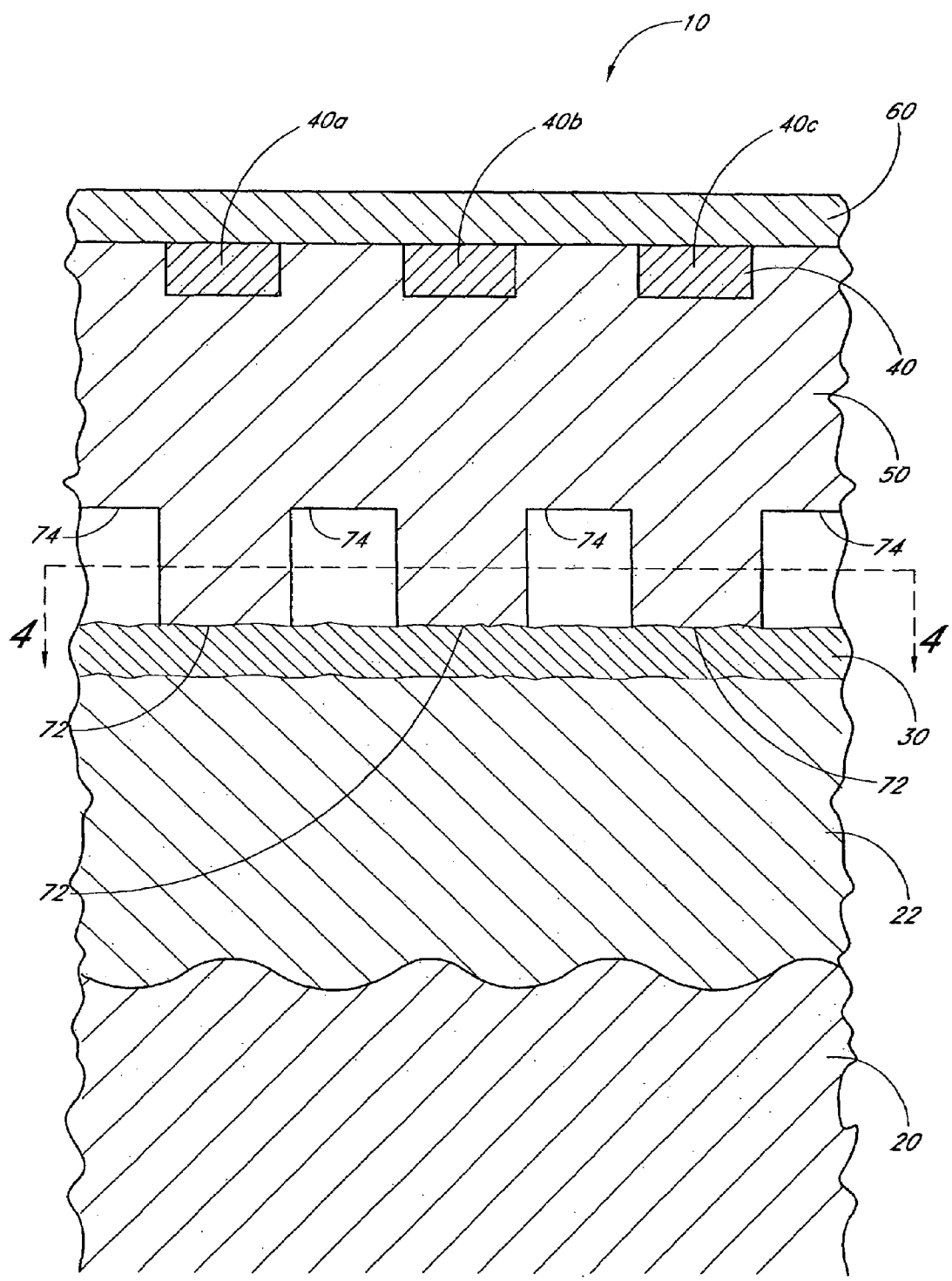
FIG. 4B schematically illustrates a fragmentary cross-sectional view taken along the lines 2-2 of FIG. 1, showing an embodiment of a portion of a therapy apparatus comprising a plurality of light sources and an element with portions contacting the scalp and portions spaced away from the scalp.

FIGS. 4A and 4B schematically illustrate embodiments of the element 50 adapted to facilitate the blanching of the scalp 30. In the cross-sectional view of a portion of the therapy apparatus 10 schematically illustrated in FIG. 4A, certain element portions 72 contact the patient's scalp 30 and other element portions 74 are spaced away from the scalp 30. The element portions 72 contacting the scalp 30 provide an optical path for light to propagate from the light source 40 to the scalp 30. The element portions 72 contacting the scalp 30 also apply pressure to the scalp 30, thereby forcing blood out from beneath the element portion 72. FIG. 4B schematically illustrates a similar view of an embodiment in which the light source 40 comprises a plurality of light sources 40a, 40b, 40c.

Figure 5A:
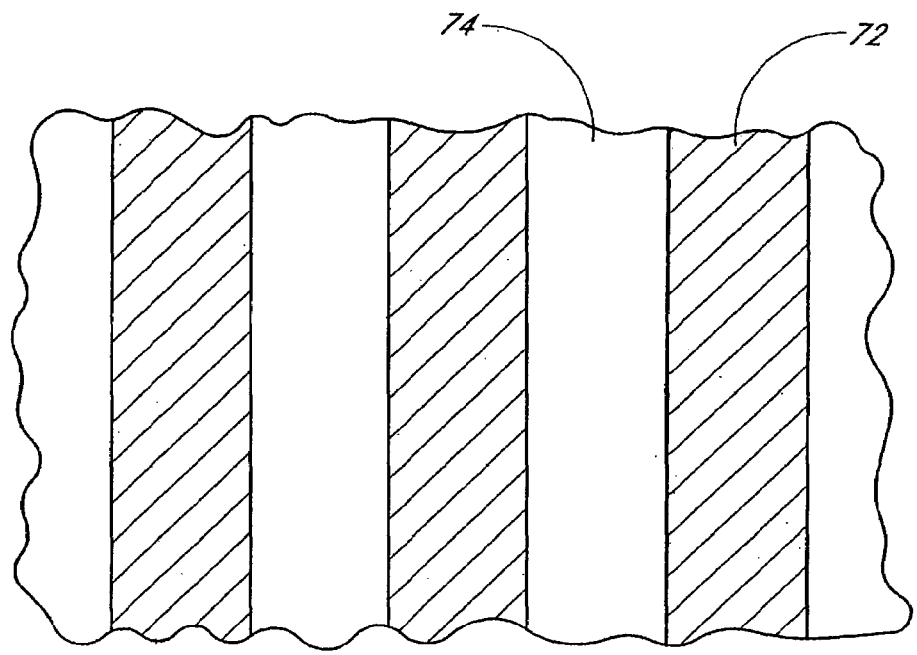
FIGS. 5A and 5B schematically illustrate cross-sectional views of two embodiments of the element in accordance with FIG. 4B taken along the line 4-4.
Figure 5B:
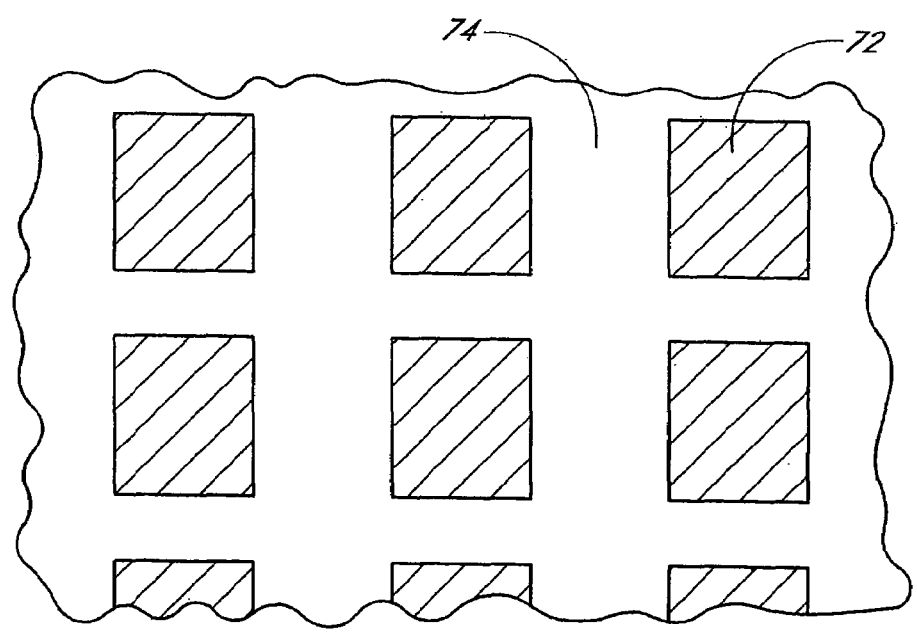

FIG. 5A schematically illustrates one embodiment of the cross-section along the line 4-4 of FIG. 4B. The element portions 72 contacting the scalp 30 comprise ridges extending along one direction, and the element portions 74 spaced away from the scalp 30 comprise troughs extending along the same direction. In certain embodiments, the ridges are substantially parallel to one another and the troughs are substantially parallel to one another. FIG. 5B schematically illustrates another embodiment of the cross-section along the line 4-4 of FIG. 4B. The element portions 72 contacting the scalp 30 comprise a plurality of projections in the form of a grid or array. More specifically, the portions 72 are rectangular and are separated by element portions 74 spaced away from the scalp 30, which form troughs extending in two substantially perpendicular directions. The portions 72 of the element 50 contacting the scalp 30 can be a substantial fraction of the total area of the element 50 or of the scalp 30.

Figure 6A:
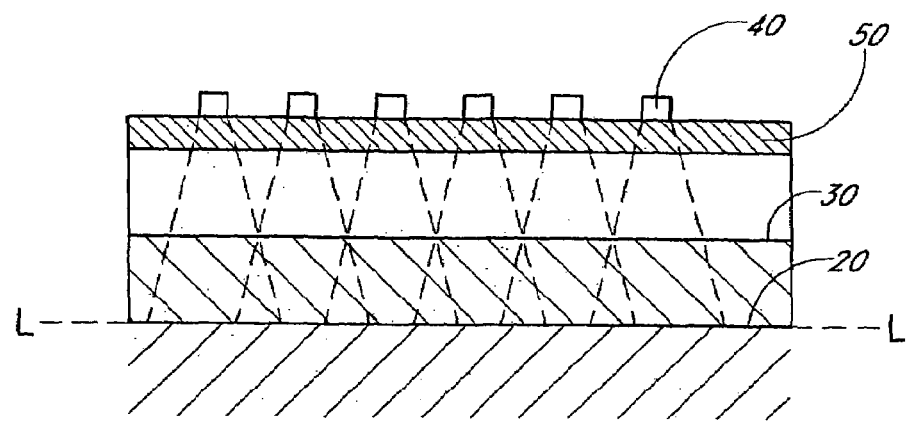
FIGS. 6A-6C schematically illustrate an embodiment in which the light sources are spaced away from the scalp.
Figure 6B:
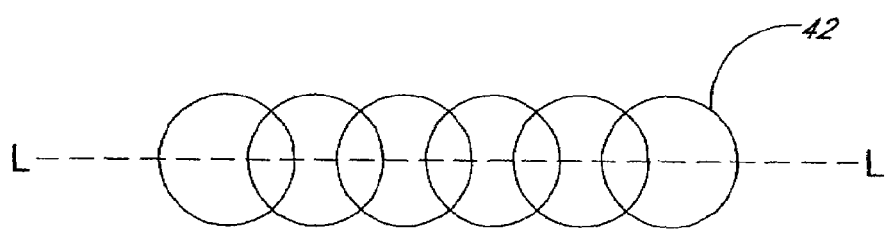
Figure 6C:
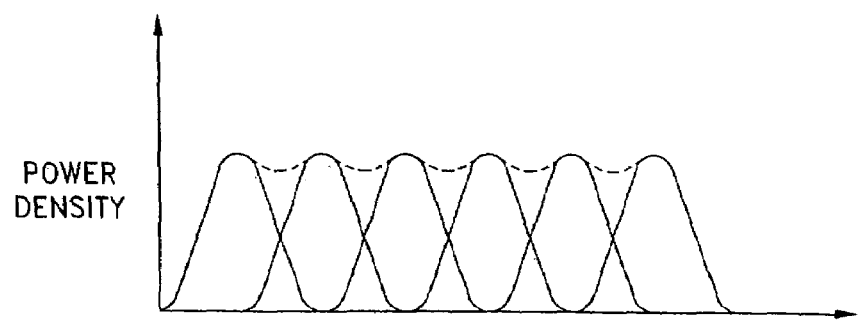

FIGS. 6A-6C schematically illustrate an embodiment in which the light sources 40 are spaced away from the scalp 30. In certain such embodiments, the light emitted by the light sources 40 propagates from the light sources 40 through the scalp 30 to the brain 20 and disperses in a direction generally parallel to the scalp 30, as shown in FIG. 6A. The light sources 40 are preferably spaced sufficiently far apart from one another such that the light emitted from each light source 40 overlaps with the light emitted from the neighboring light sources 40 at the brain 20. FIG. 6B schematically illustrates this overlap as the overlap of circular spots 42 at a reference depth at or below the surface of the brain 20. FIG. 6C schematically illustrates this overlap as a graph of the power density at the reference depth of the brain 20 along the line L-L of FIGS. 6A and 6B. Summing the power densities from the neighboring light sources 40 (shown as a dashed line in FIG. 6C) serves to provide a more uniform light distribution at the tissue to be treated. In such embodiments, the summed power density is preferably less than a damage threshold of the brain 20 and above an efficacy threshold.

Figure 7A:
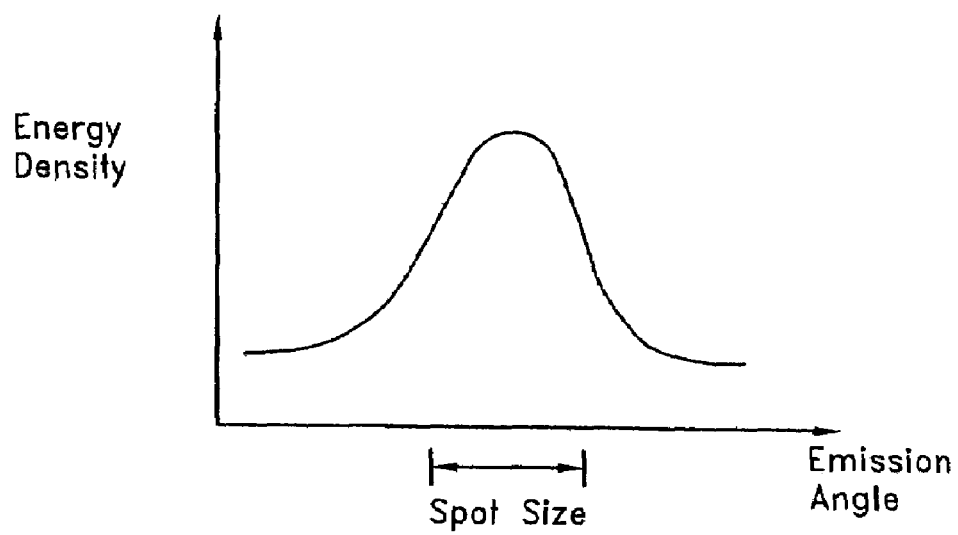
FIGS. 7A and 7B schematically illustrate the diffusive effect on the light by the element.
Figure 7B:
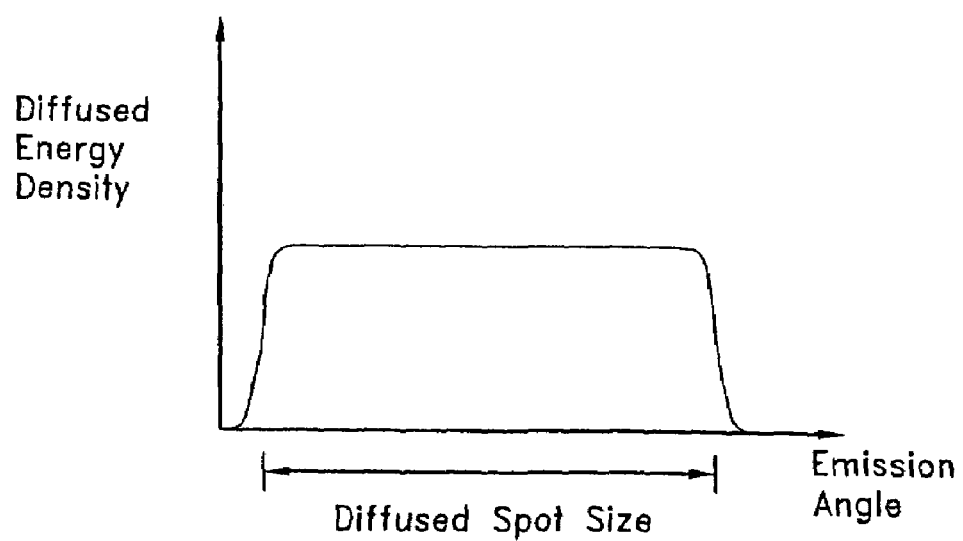

In certain embodiments, the element 50 is adapted to diffuse the light prior to reaching the scalp 30. FIGS. 7A and 7B schematically illustrate the diffusive effect on the light by the element 50. An exemplary energy density profile of the light emitted by a light source 40, as illustrated by FIG. 7A, is peaked at a particular emission angle. After being diffused by the element 50, as illustrated by FIG. 7B, the energy density profile of the light does not have a substantial peak at any particular emission angle, but is substantially evenly distributed among a range of emission angles. By diffusing the light emitted by the light source 40, the element 50 distributes the light energy substantially evenly over the area to be illuminated, thereby inhibiting "hot spots" which would otherwise create temperature increases at the scalp 30. In addition, by diffusing the light prior to its reaching the scalp 30, the element 50 can effectively increase the spot size of the light impinging the scalp 30, thereby advantageously lowering the power density at the scalp 30, as described more fully below. In addition, in embodiments with multiple light sources 40, the element 50 can diffuse the light to alter the total light output distribution to reduce inhomogeneities.

In certain embodiments, the element 50 provides sufficient diffusion of the light such that the power density of the light is less than a maximum tolerable level of the scalp 30 and brain 20. In certain other embodiments, the element 50 provides sufficient diffusion of the light such that the power density of the light equals a therapeutic value at the target tissue. The element 50 can comprise exemplary diffusers including, but are not limited to, holographic diffusers such as those available from Physical Optics Corp. of Torrance, Calif. and Display Optics P/N SN1333 from Reflexite Corp. of Avon, Conn.

Power Density

Phototherapy for the treatment of depression is based in part on the discovery that power density (i.e., power per unit area or number of photons per unit area per unit time) and energy density (i.e., energy per unit area or number of photons per unit area) of the light energy applied to tissue appear to be significant factors in determining the relative efficacy of low level phototherapy. Preferred methods described herein are based at least in part on the finding that, given a selected wavelength of light energy, it is the power density and/or the energy density of the light delivered to tissue (as opposed to the total power or total energy delivered to the tissue) that appears to be an important factor in determining the relative efficacy of phototherapy.

Without being bound by theory, it is believed that light energy delivered within a certain range of power densities and energy densities provides the desired biostimulative effect on the intracellular environment, such that upregulation of neurotrophic factors occurs which results in neurogenesis, the growth of existing neurons and the possible growth of new neurons, as well as supporting plasticity in neural functioning, including at the synapse level, the suppression of which is thought to be instrumental in depression. It is further believed that the light energy may assist in the regulation of one or more neurotransmitters, including increasing the level of serotonin and/or norepinephrine, so that a more normal balance of neurotransmitters is achieved. The biostimulative effect may include stimulation of the mitochondria by interaction of the light with chromophores within the target tissue, which facilitate production of ATP thereby feeding energy to injured or stressed cells. Further information regarding the role of power density and exposure time is described by Hans H. F. I. van Breugel and P. R. Dop Bär in "Power Density and Exposure Time of He-Ne Laser Irradiation Are More Important Than Total Energy Dose in Photo-Biomodulation of Human Fibroblasts In Vitro," Lasers in Surgery and Medicine, Volume 12, pp. 528-537 (1992), which is incorporated in its entirety by reference herein.

Figure 8B:
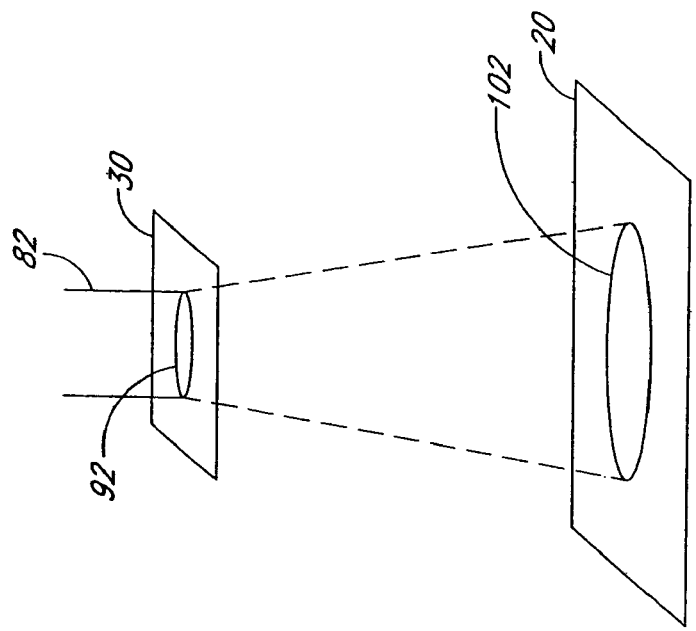
FIGS. 8A and 8B schematically illustrate two light beams having different cross-sections impinging a patient's scalp and propagating through the patient's head to irradiate a portion of the patient's brain tissue.
Figure 8A:
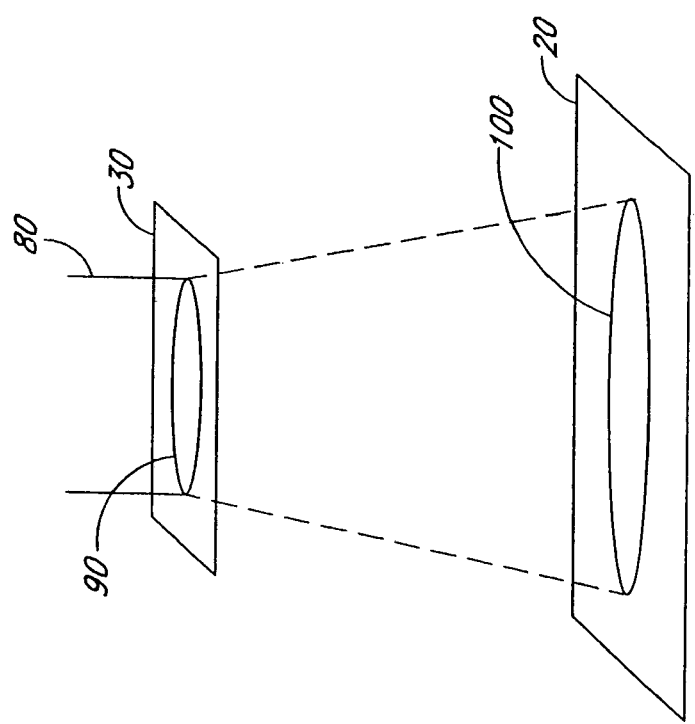

The significance of the power density used in phototherapy has ramifications with regard to the devices and methods used in phototherapy of brain tissue, as schematically illustrated by FIGS. 8A and 8B, which show the effects of scattering by intervening tissue. Further information regarding the scattering of light by tissue is provided by V. Tuchin in "Tissue Optics: Light Scattering Methods and Instruments for Medical Diagnosis," SPIE Press (2000), Bellingham, Wash., pp. 3-11, which is incorporated in its entirety by reference herein.

FIG. 8A schematically illustrates a light beam 80 impinging a portion 90 of a patient's scalp 30 and propagating through the patient's head to irradiate a portion 100 of the patient's brain tissue 20. In the exemplary embodiment of FIG. 8A, the light beam 80 impinging the scalp 30 is collimated and has a circular cross-section with a radius of 2 cm and a cross-sectional area of approximately 12.5 $cm^2$. For comparison purposes, FIG. 8B schematically illustrates a light beam 82 having a significantly smaller cross-section impinging a smaller portion 92 of the scalp 30 to irradiate a portion 102 of the brain tissue 20. The light beam 82 impinging the scalp 30 in FIG. 8B is collimated and has a circular cross-section with a radius of 1 cm and a cross-sectional area of approximately 3.1 $cm^2$. The collimations, cross-sections, and radii of the light beams 80, 82 illustrated in FIGS. 8A and 8B are exemplary; other light beams with other parameters are also compatible with embodiments described herein. In particular, similar considerations apply to focussed beams or diverging beams, as they are similarly scattered by the intervening tissue.

As shown in FIGS. 8A and 8B, the cross-sections of the light beams 80, 82 become larger while propagating through the head due to scattering from interactions with tissue of the head. Assuming that the angle of dispersion is 15 degrees and the irradiated brain tissue 20 is 2.5 cm below the scalp 30, the resulting area of the portion 100 of brain tissue 20 irradiated by the light beam 80 in FIG. 8A is approximately 22.4 $cm^2$. Similarly, the resulting area of the portion 102 of brain tissue 20 irradiated by the light beam 82 in FIG. 8B is approximately 8.8 $cm^2$.

Irradiating the portion 100 of the brain tissue 20 with a power density of 10 $mW/cm^2$ corresponds to a total power within the portion 100 of approximately 224 mW (10 $mW/cm^2 \times 22.4\ cm^2$). Assuming only approximately 5% of the light beam 80 is transmitted between the scalp 30 and the brain tissue 20, the incident light beam 80 at the scalp 30 will have a total power of approximately 4480 mW (224 mW/0.05) and a power density of approximately 358 $mW/cm^2$ (4480 mW/12.5 $cm^2$). Similarly, irradiating the portion 102 of the brain tissue 20 with a power density of 10 $mW/cm^2$ corresponds to a total power within the portion 102 of approximately 88 mW (10 $mW/cm^2 \times 8.8\ cm^2$), and with the same 5% transmittance, the incident light beam 82 at the scalp 30 will have a total power of approximately 1760 mW (88 mW/0.05) and a power density of approximately 568 $mW/cm^2$ (1760 mW/3.1 $cm^2$). These calculations are summarized in Table 1.

TABLE 1

|  | 2 cm Spot Size (FIG. 8A) | 1 cm Spot Size (FIG. 8B) |
|---|---|---|
| Scalp: | | |
| Area | 12.5 $cm^2$ | 3.1 $cm^2$ |
| Total power | 4480 mW | 1760 mW |
| Power density | 358 $mW/cm^2$ | 568 $mW/cm^2$ |
| Brain: | | |
| Area | 22.4 $cm^2$ | 8.8 $cm^2$ |
| Total power | 224 mW | 88 mW |
| Power density | 10 $mW/cm^2$ | 10 $mW/cm^2$ |

These exemplary calculations illustrate that to obtain a desired power density at the brain 20, higher total power at the scalp 30 can be used in conjunction with a larger spot size at the scalp 30. Thus, by increasing the spot size at the scalp 30, a desired power density at the brain 20 can be achieved with lower power densities at the scalp 30 which can reduce the possibility of overheating the scalp 30. In certain embodiments, the light can be directed through an aperture to define the illumination of the scalp 30 to a selected smaller area.

Light Source

The light source 40 preferably generates light in the visible to near-infrared wavelength range. In certain embodiments, the light source 40 comprises one or more laser diodes, which each provide coherent light. In embodiments in which the light from the light source 40 is coherent, the emitted light may produce "speckling" due to coherent interference of the light. This speckling comprises intensity spikes which are created by constructive interference and can occur in proximity to the target tissue being treated. For example, while the average power density may be approximately 10 mW/cm$^2$, the power density of one such intensity spike in proximity to the brain tissue to be treated may be approximately 300 mW/cm$^2$. In certain embodiments, this increased power density due to speckling can improve the efficacy of treatments using coherent light over those using incoherent light for illumination of deeper tissues.

In other embodiments, the light source 40 provides incoherent light. Exemplary light sources 40 of incoherent light include, but are not limited to, incandescent lamps or light-emitting diodes. A heat sink can be used with the light source 40 (for either coherent or incoherent sources) to remove heat from the light source 40 and to inhibit temperature increases at the scalp 30.

In certain embodiments, the light source 40 generates light which is substantially monochromatic (i.e., light having one wavelength, or light having a narrow band of wavelengths). So that the amount of light transmitted to the brain is maximized, the wavelength of the light is selected in certain embodiments to be at or near a transmission peak (or at or near an absorption minimum) for the intervening tissue. In certain such embodiments, the wavelength corresponds to a peak in the transmission spectrum of tissue at about 820 nanometers. In other embodiments, the wavelength of the light is preferably between about 630 nanometers and about 1064 nanometers, more preferably between about 780 nanometers and about 840 nanometers, and most preferably includes wavelengths of about 790, 800, 810, 820, or 830 nanometers. It has also been found that an intermediate wavelength of about 739 nanometers appears to be suitable for penetrating the skull, although other wavelengths are also suitable and may be used.

In other embodiments, the light source 40 generates light having a plurality of wavelengths. In certain such embodiments, each wavelength is selected so as to work with one or more chromophores within the target tissue. Without being bound by theory, it is believed that irradiation of chromophores increases the production of ATP in the target tissue, thereby producing beneficial effects. In certain embodiments, the light source 40 is adapted to generate light having a first wavelength concurrently with light having a second wavelength. In certain other embodiments, the light source 40 is adapted to generate light having a first wavelength sequentially with light having a second wavelength.

In certain embodiments, the light source 40 includes at least one continuously emitting GaAlAs laser diode having a wavelength of about 830 nanometers. In another embodiment, the light source 40 comprises a laser source having a wavelength of about 808 nanometers. In still other embodiments, the light source 40 includes at least one vertical cavity surface-emitting laser (VCSEL) diode. Other light sources 40 compatible with embodiments described herein include, but are not limited to, light-emitting diodes (LEDs) and filtered lamps.

The light source 40 is capable of emitting light energy at a power sufficient to achieve a predetermined power density at the subdermal target tissue (e.g., at a depth of approximately 2 centimeters from the dura). It is presently believed that phototherapy of tissue is most effective when irradiating the target tissue with power densities of light of at least about 0.01 mW/cm$^2$ and up to about 1 W/cm$^2$. In various embodiments, the subsurface power density is at least about 0.01, 0.05, 0.1, 0.5, 1, 5, 10, 15, 20, 30, 40, 50, 60, 70, 80, or 90 mW/cm$^2$, respectively, depending on the desired clinical performance. In certain embodiments, the subsurface power density is preferably about 0.01 mW/cm$^2$ to about 100 mW/cm$^2$, more preferably about 0.01 mW/cm$^2$ to about 50 mW/cm$^2$, and most preferably about 2 mW/cm$^2$ to about 20 mW/cm$^2$. It is believed that these subsurface power densities are especially effective at producing the desired biostimulative effects on the tissue being treated.

Taking into account the attenuation of energy as it propagates from the skin surface, through body tissue, bone, and fluids, to the subdermal target tissue, surface power densities preferably between about 10 mW/cm$^2$ to about 10 W/cm$^2$, or more preferably between about 100 mW/cm$^2$ to about 500 mW/cm$^2$, will typically be used to attain the selected power densities at the subdermal target tissue. To achieve such surface power densities, the light source 40 is preferably capable of emitting light energy having a total power output of at least about 25 mW to about 100 W. In various embodiments, the total power output is limited to be no more than about 30, 50, 75, 100, 150, 200, 250, 300, 400, or 500 mW, respectively. In certain embodiments, the light source 40 comprises a plurality of sources used in combination to provide the total power output. The actual power output of the light source 40 is preferably controllably variable. In this way, the power of the light energy emitted can be adjusted in accordance with a selected power density at the subdermal tissue being treated.

Certain embodiments utilize a light source 40 that includes only a single laser diode that is capable of providing about 25 mW to about 100 W of total power output at the skin surface. In certain such embodiments, the laser diode can be optically coupled to the scalp 30 via an optical fiber or can be configured to provide a sufficiently large spot size to avoid power densities which would burn or otherwise damage the scalp 30. In other embodiments, the light source 40 utilizes a plurality of sources (e.g., laser diodes) arranged in a grid or array that together are capable of providing at least about 25 mW to about 100 W of total power output at the skin surface. The light source 40 of other embodiments may also comprise sources having power capacities outside of these limits.

Figure 9A:
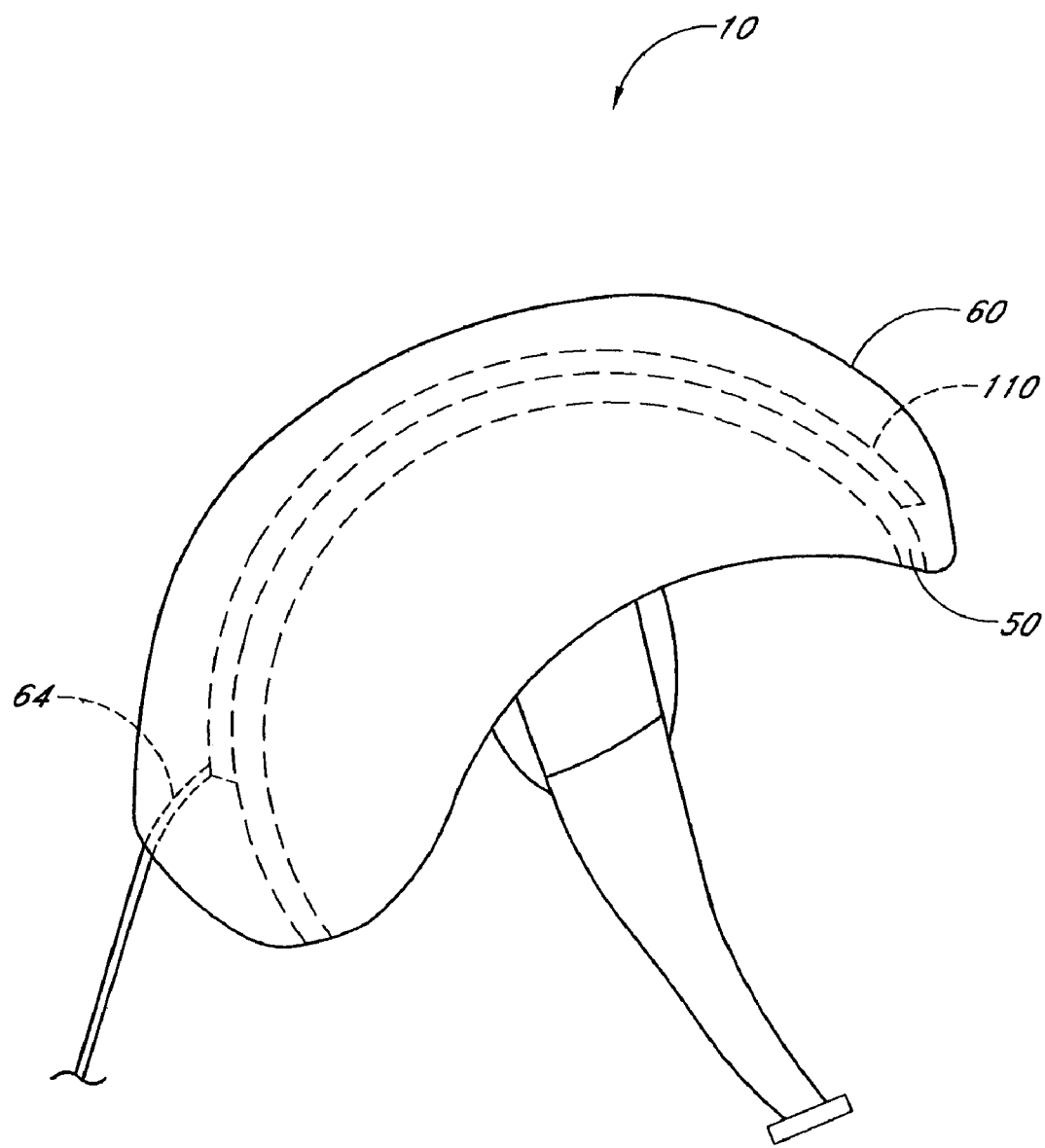
FIG. 9A schematically illustrates a therapy apparatus comprising a cap and a light source comprising a light blanket.
Figure 9B:
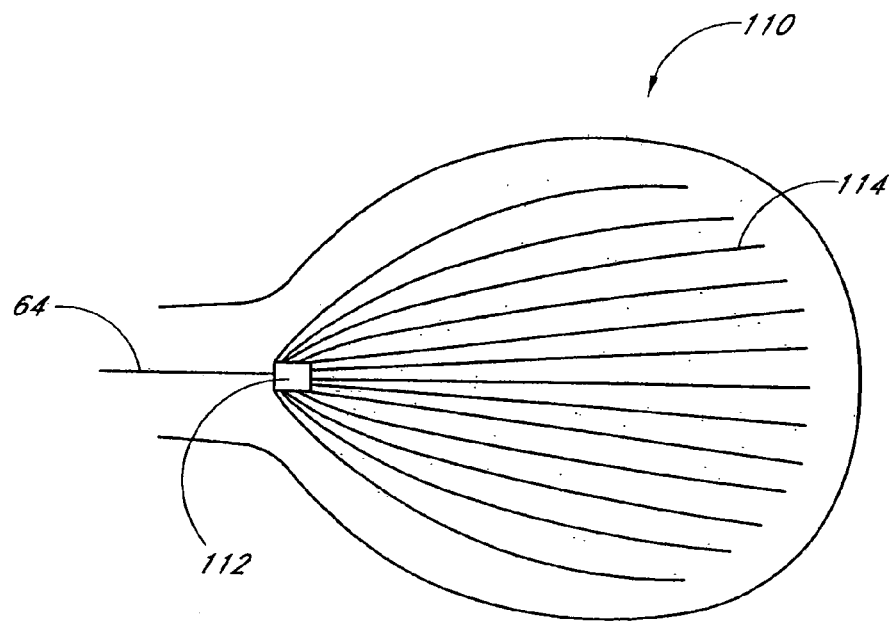
FIGS. 9B and 9C schematically illustrate two embodiments of the light blanket.
Figure 9C:
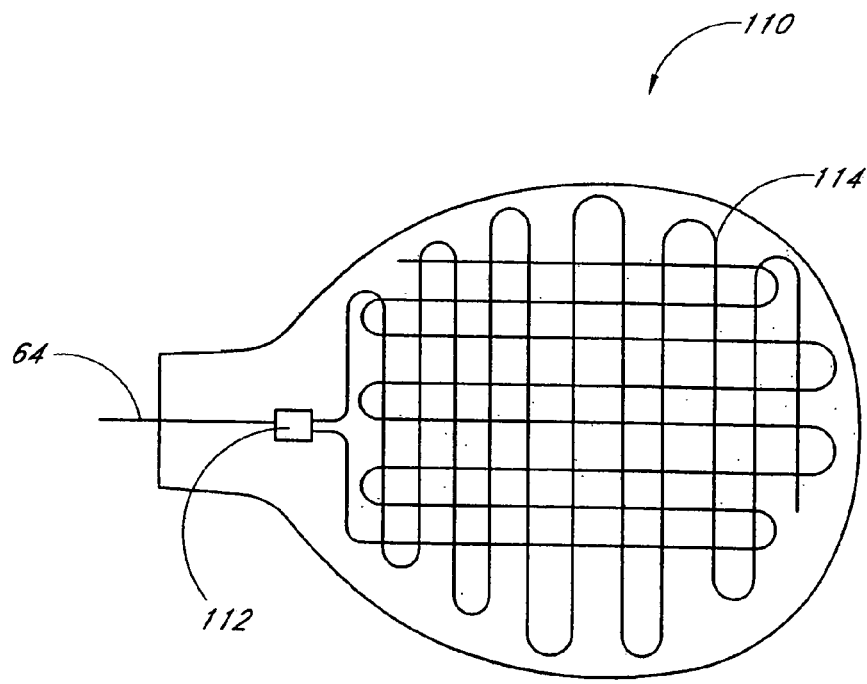

FIG. 9A schematically illustrates another embodiment of the therapy apparatus 10 which comprises the cap 60 and a light source comprising a light-emitting blanket 110. FIG. 9B schematically illustrates an embodiment of the blanket 110 comprising a flexible substrate 111 (e.g., flexible circuit board), a power conduit interface 112, and a sheet formed by optical fibers 114 positioned in a fan-like configuration. FIG. 9C schematically illustrates an embodiment of the blanket 110 comprising a flexible substrate 111, a power conduit interface 112, and a sheet formed by optical fibers 114 woven into a mesh. The blanket 110 is preferably positioned within the cap 60 so as to cover an area of the scalp 30 corresponding to a portion of the brain 20 to be treated.

In certain such embodiments, the power conduit interface 112 is adapted to be coupled to an optical fiber conduit 64 which provides optical power to the blanket 110. The optical power interface 112 of certain embodiments comprises a beam splitter or other optical device which distributes the incoming optical power among the various optical fibers 114. In other embodiments, the power conduit interface 112 is adapted to be coupled to an electrical conduit which provides electrical power to the blanket 110. In certain such embodiments, the power conduit interface 112 comprises one or more laser diodes, the output of which is distributed among the various optical fibers 114 of the blanket 110. In certain other embodiments, the blanket 110 comprises an electroluminescent sheet which responds to electrical signals from the power conduit interface 112 by emitting light. In such embodiments, the power conduit interface 112 comprises circuitry adapted to distribute the electrical signals to appropriate portions of the electroluminescent sheet.

The side of the blanket 110 nearer the scalp 30 is preferably provided with a light scattering surface, such as a roughened surface to increase the amount of light scattered out of the blanket 110 towards the scalp 30. The side of the blanket 110 further from the scalp 30 is preferably covered by a reflective coating so that light emitted away from the scalp 30 is reflected back towards the scalp 30. This configuration is similar to configurations used for the "back illumination" of liquid-crystal displays (LCDs). Other configurations of the blanket 110 are compatible with embodiments described herein.

In certain embodiments, the light source 40 generates light which cause eye damage if viewed by an individual. In such embodiments, the apparatus 50 can be configured to provide eye protection so as to avoid viewing of the light by individuals. For example, opaque materials can be appropriately placed to block the light from being viewed directly. In addition, interlocks can be provided so that the light source 40 is not activated unless the apparatus 50 is in place, or other appropriate safety measures are taken.

Light Delivery Apparatuses

The phototherapy methods for the treatment of depression described herein may be practiced and described using, for example, a low level laser therapy apparatus such as that shown and described in U.S. Pat. No. 6,214,035, U.S. Pat. No. 6,267,780, U.S. Pat. No. 6,273,905 and U.S. Pat. No. 6,290,714, which are all incorporated in their entirety by reference herein, as are the references incorporated by reference therein.

Figure 10:
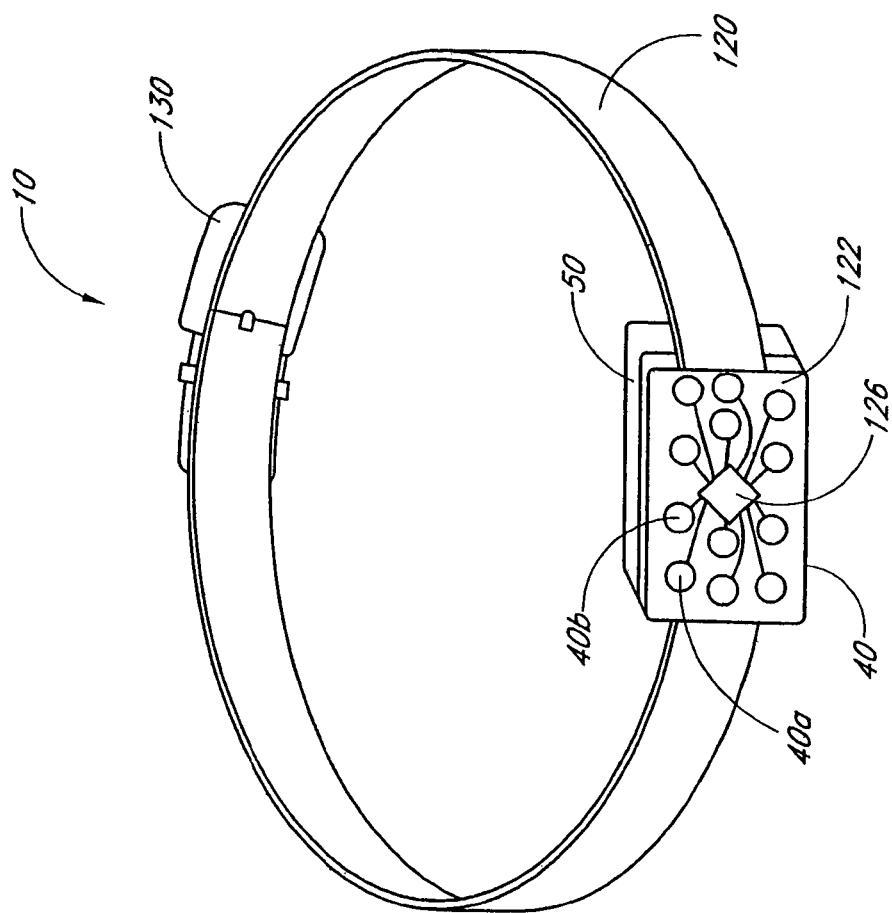
FIG. 10 schematically illustrates a therapy apparatus comprising a flexible strap and a housing.

Another suitable phototherapy apparatus in accordance with embodiments described here is illustrated in FIG. 10. The illustrated therapy apparatus 10 includes a light source 40, an element 50, and a flexible strap 120 adapted for securing the therapy apparatus 10 over an area of the patient's head. The light source 40 can be disposed on the strap 120 itself, or in a housing 122 coupled to the strap 120. The light source 40 preferably comprises a plurality of diodes 40a, 40b, capable of emitting light energy having a wavelength in the visible to near-infrared wavelength range. The element 50 is adapted to be positioned between the light source 40 and the patient's scalp 30.

The therapy apparatus 10 further includes a power supply (not shown) operatively coupled to the light source 40, and a programmable controller 126 operatively coupled to the light source 40 and to the power supply. The programmable controller 126 is configured to control the light source 40 so as to deliver a predetermined power density to the brain tissue 20. In certain embodiments, as schematically illustrated in FIG. 10, the light source 40 comprises the programmable controller 126. In other embodiments the programmable controller 126 is a separate component of the therapy apparatus 10.

In certain embodiments, the strap 120 comprises a loop of elastomeric material sized appropriately to fit snugly onto the patient's scalp 30. In other embodiments, the strap 120 comprises an elastomeric material to which is secured any suitable securing means 130, such as mating Velcro strips, buckles, snaps, hooks, buttons, ties, or the like. The precise configuration of the strap 120 is subject only to the limitation that the strap 120 is capable of maintaining the light source 40 in a selected position so that light energy emitted by the light source 40 is directed towards the targeted brain tissue 20.

In the exemplary embodiment illustrated in FIG. 10, the housing 122 comprises a layer of flexible plastic or fabric that is secured to the strap 120. In other embodiments, the housing 122 comprises a plate or an enlarged portion of the strap 120. Various strap configurations and spatial distributions of the light sources 40 are compatible with embodiments described herein so that the therapy apparatus 10 can treat selected portions of brain tissue.

Figure 11:
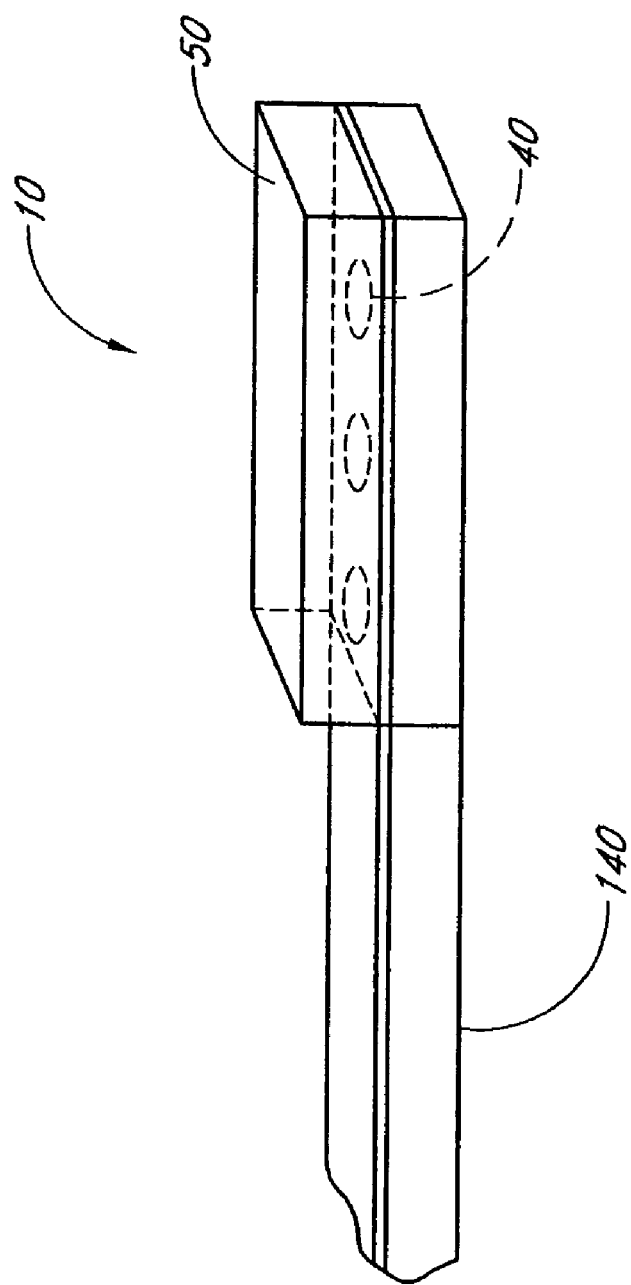
FIG. 11 schematically illustrates a therapy apparatus comprising a handheld probe.

In still other embodiments, the therapy apparatus 10 for delivering the light energy includes a handheld probe 140, as schematically illustrated in FIG. 11. The probe 140 includes a light source 40 and an element 50 as described herein.

Figure 12:
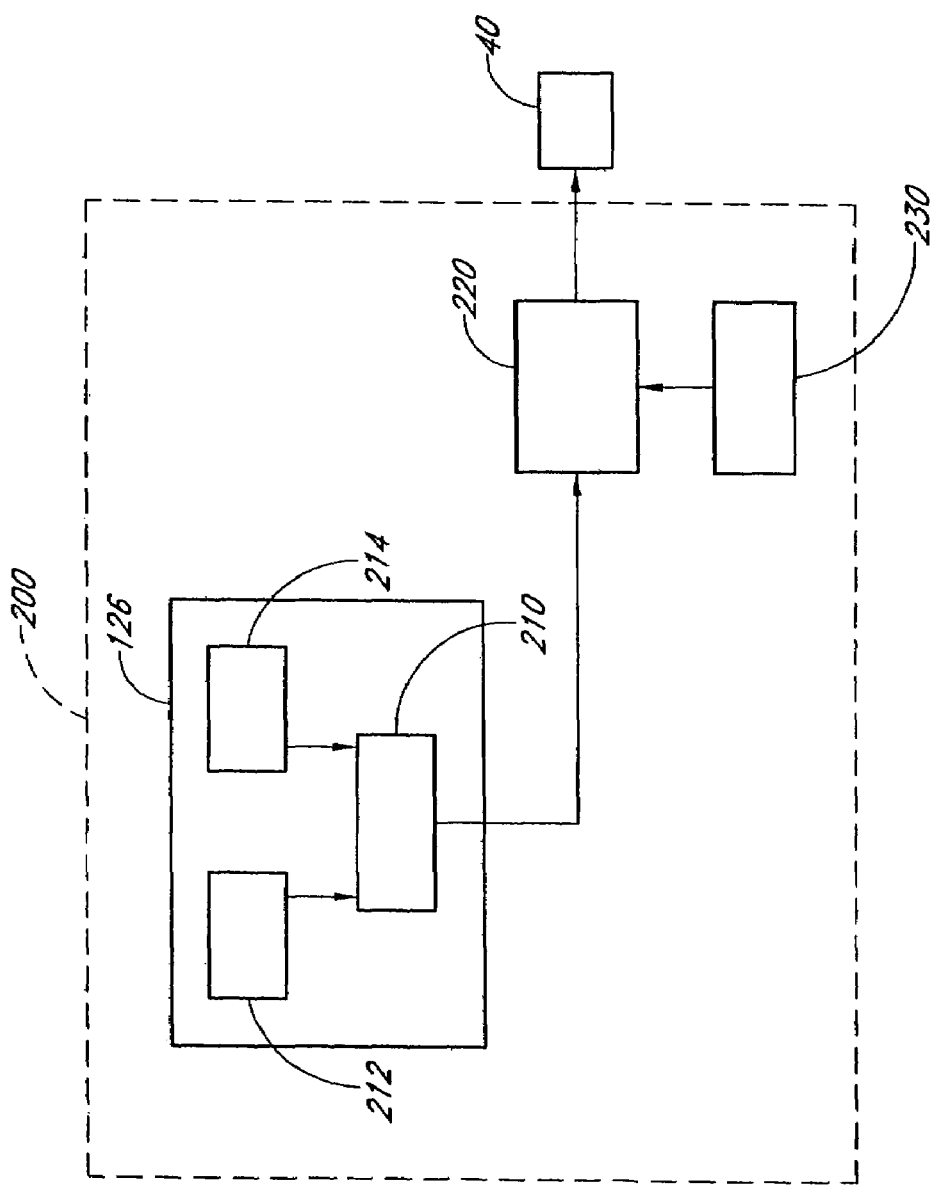
FIG. 12 is a block diagram of a control circuit comprising a programmable controller.

FIG. 12 is a block diagram of a control circuit 200 comprising a programmable controller 126 according to embodiments described herein. The control circuit 200 is configured to adjust the power of the light energy emitted by the light source 40 to generate a predetermined surface power density at the scalp 30 corresponding to a predetermined energy delivery profile, such as a predetermined subsurface power density, to the target area of the brain 20.

In certain embodiments, the programmable controller 126 comprises a logic circuit 210, a clock 212 coupled to the logic circuit 210, and an interface 214 coupled to the logic circuit 210. The clock 212 of certain embodiments provides a timing signal to the logic circuit 210 so that the logic circuit 210 can monitor and control timing intervals of the applied light. Examples of timing intervals include, but are not limited to, total treatment times, pulsewidth times for pulses of applied light, and time intervals between pulses of applied light. In certain embodiments, the light sources 40 can be selectively turned on and off to reduce the thermal load on the scalp 30 and to deliver a selected power density to particular areas of the brain 20.

The interface 214 of certain embodiments provides signals to the logic circuit 210 which the logic circuit 210 uses to control the applied light. The interface 214 can comprise a user interface or an interface to a sensor monitoring at least one parameter of the treatment. In certain such embodiments, the programmable controller 126 is responsive to signals from the sensor to preferably adjust the treatment parameters to optimize the measured response. The programmable controller 126 can thus provide closed-loop monitoring and adjustment of various treatment parameters to optimize the phototherapy. The signals provided by the interface 214 from a user are indicative of parameters that may include, but are not limited to, patient characteristics (e.g., skin type, fat percentage), selected applied power densities, target time intervals, and power density/timing profiles for the applied light.

In certain embodiments, the logic circuit 210 is coupled to a light source driver 220. The light source driver 220 is coupled to a power supply 230, which in certain embodiments comprises a battery and in other embodiments comprises an alternating current source. The light source driver 220 is also coupled to the light source 40. The logic circuit 210 is responsive to the signal from the clock 212 and to user input from the user interface 214 to transmit a control signal to the light source driver 220. In response to the control signal from the logic circuit 210, the light source driver 220 adjust and controls the power applied to the light sources 40. Other control circuits besides the control circuit 200 of FIG. 12 are compatible with embodiments described herein.

In certain embodiments, the logic circuit 110 is responsive to signals from a sensor monitoring at least one parameter of the treatment to control the applied light. For example, certain embodiments comprise a temperature sensor thermally coupled to the scalp 30 to provide information regarding the temperature of the scalp 30 to the logic circuit 210. In such embodiments, the logic circuit 210 is responsive to the information from the temperature sensor to transmit a control signal to the light source driver 220 so as to adjust the parameters of the applied light to maintain the scalp temperature below a predetermined level. Other embodiments include exemplary biomedical sensors including, but not limited to, a blood flow sensor, a blood gas (e.g., oxygenation) sensor, an ATP production sensor, or a cellular activity sensor. Such biomedical sensors can provide real-time feedback information to the logic circuit 210. In certain such embodiments, the logic circuit 110 is responsive to signals from the sensors to preferably adjust the parameters of the applied light to optimize the measured response. The logic circuit 110 can thus provide closed-loop monitoring and adjustment of various parameters of the applied light to optimize the phototherapy.

Figure 13:
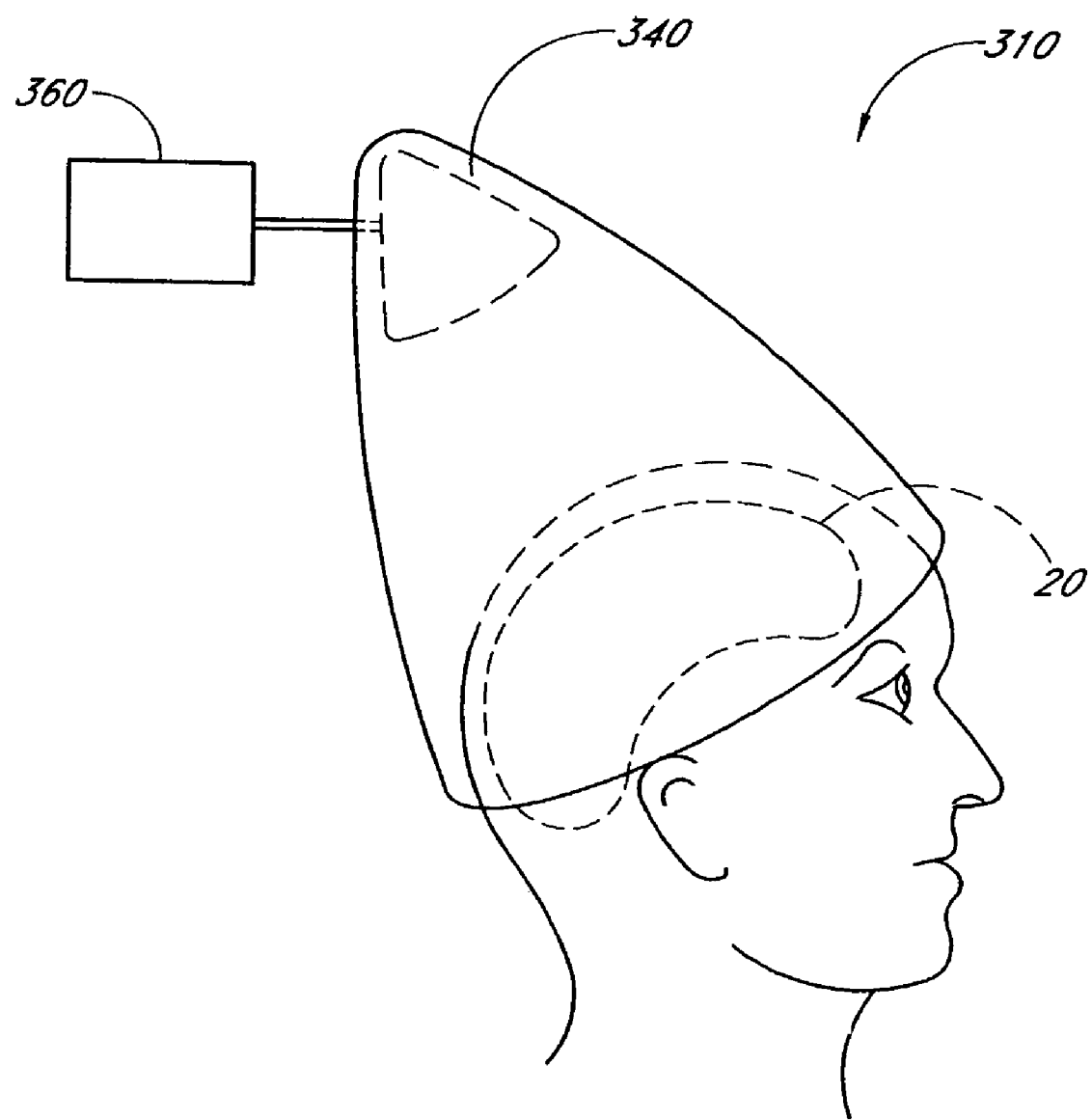
FIG. 13 schematically illustrates a therapy apparatus comprising a light source and a controller.

In certain embodiments, as schematically illustrated in FIG. 13, the therapy apparatus 310 comprises a light source 340 adapted to irradiate a portion of the patient's brain 20 with an efficacious power density and wavelength of light. The therapy apparatus 310 further comprises a controller 360 for energizing said light source 340, so as to selectively produce a plurality of different irradiation patterns on the patient's scalp 30. Each of the irradiation patterns is comprised of a least one illuminated area that is small compared to the patient's scalp 30, and at least one non-illuminated area.

Figure 14:
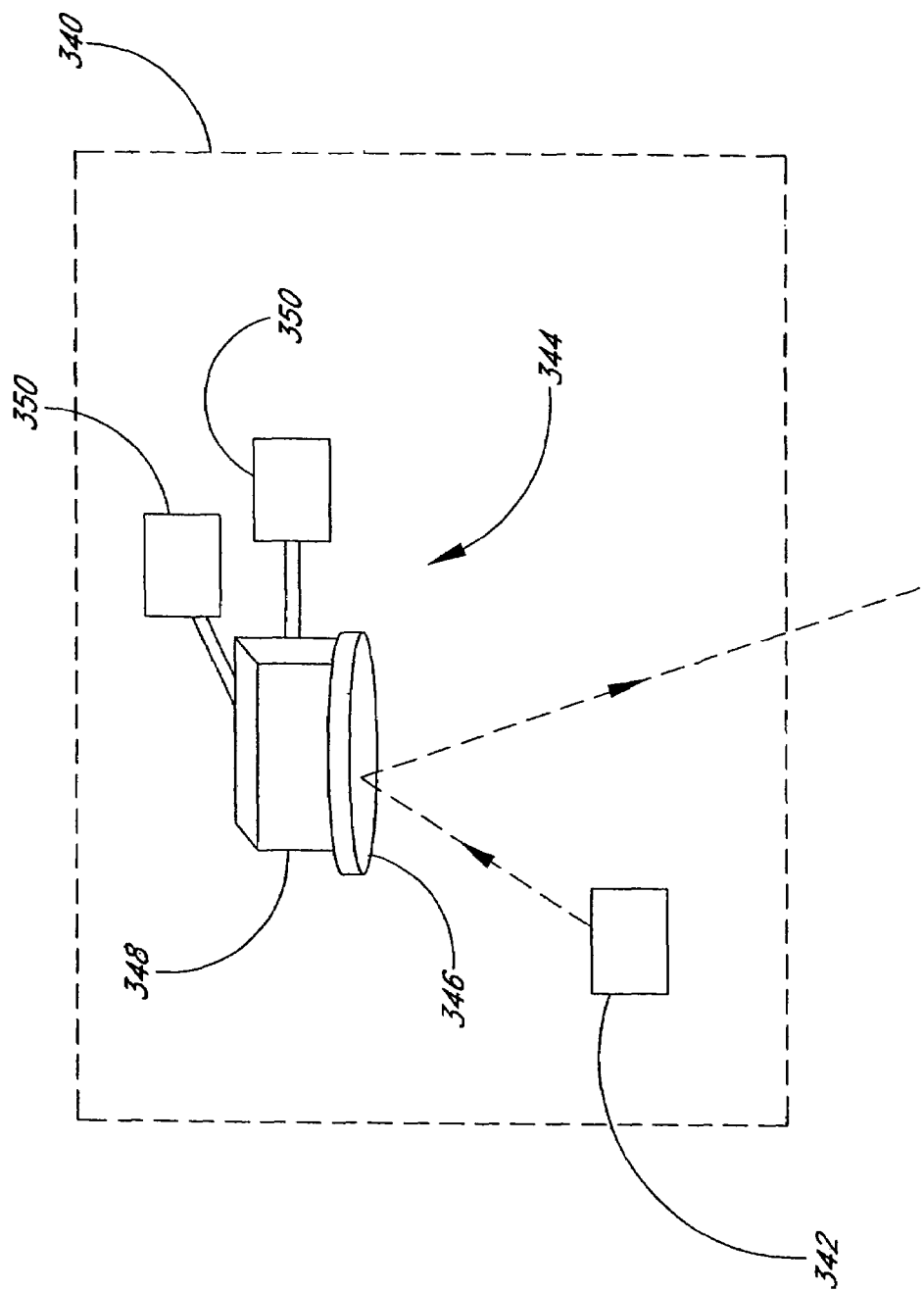
FIG. 14 schematically illustrates a light source comprising a laser diode and a galvometer with a mirror and a plurality of motors.

In certain embodiments, the light source 340 includes an apparatus for adjusting the emitted light to irradiate different portions of the scalp 30. In certain such embodiments, the apparatus physically moves the light source 40 relative to the scalp 30. In other embodiments, the apparatus does not move the light source 40, but redirects the emitted light to different portions of the scalp 30. In an exemplary embodiment, as schematically illustrated in FIG. 14, the light source 340 comprises a laser diode 342 and a galvometer 344, both of which are electrically coupled to the controller 360. The galvometer 344 comprises a mirror 346 mounted onto an assembly 348 which is adjustable by a plurality of motors 350. Light emitted by the laser diode 342 is directed toward the mirror 346 and is reflected to selected portions of the patient's scalp 30 by selectively moving the mirror 346 and selectively activating the laser diode 342. In certain embodiments, the therapy apparatus 310 comprises an element 50 adapted to inhibit temperature increases at the scalp 30 as described herein.

Figure 15A:
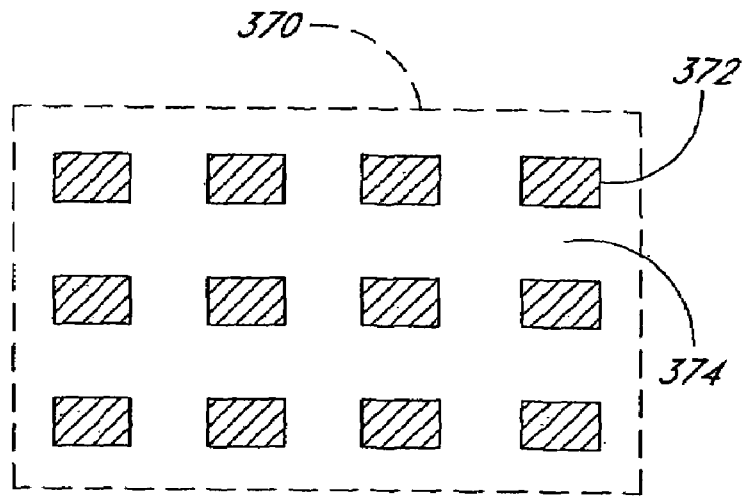
FIGS. 15A and 15B schematically illustrate two irradiation patterns that are spatially shifted relative to each other.

FIG. 15A schematically illustrates an irradiation pattern 370 in accordance with embodiments described herein. The irradiation pattern 370 comprises at least one illuminated area 372 and at least one non-illuminated area 374. In certain embodiments, the irradiation pattern 370 is generated by scanning the mirror 346 so that the light impinges the patient's scalp 30 in the illuminated area 372 but not in the non-illuminated area 374. Certain embodiments modify the illuminated area 372 and the non-illuminated area 374 as a function of time.

Figure 15B:
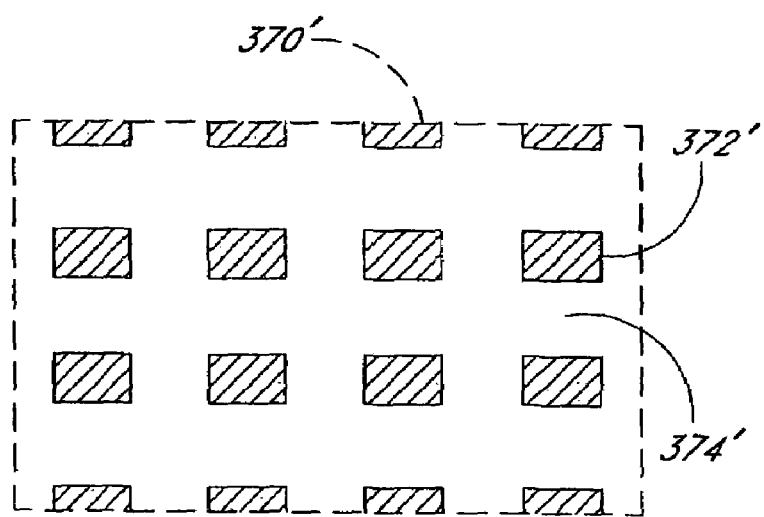

This selective irradiation can be used to reduce the thermal load on particular locations of the scalp 30 by moving the light from one illuminated area 372 to another. For example, by irradiating the scalp 30 with the irradiation pattern 370 schematically illustrated in FIG. 15A, the illuminated areas 372 of the scalp 30 are heated by interaction with the light, and the non-illuminated areas 374 are not heated. By subsequently irradiating the scalp 30 with the complementary irradiation pattern 370' schematically illustrated in FIG. 15B, the previously non-illuminated areas 374 are now illuminated areas 372', and the previously illuminated areas 372 are now non-illuminated areas 374'. A comparison of the illuminated areas 372 of the irradiation pattern 370 of FIG. 15A with the illuminated area 372' of the irradiation pattern 370' of FIG. 15B shows that the illuminated areas 372, 372' do not significantly overlap one another. In this way, the thermal load at the scalp 30 due to the absorption of the light can be distributed across the scalp 30, thereby avoiding unduly heating one or more portions of the scalp 30.

Methods of Light Delivery

Preferred methods of phototherapy are based at least in part on the finding described above that, for a selected wavelength, the power density (light intensity or power per unit area, in $W/cm^2$) or the energy density (energy per unit area, in $J/cm^2$, or power density multiplied by the exposure time) of the light energy delivered to tissue is an important factor in determining the relative efficacy of the phototherapy, and efficacy is not as directly related to the total power or the total energy delivered to the tissue. In the methods described herein, power density or energy density as delivered to a portion of the patient's brain 20, including but not limited to the cortex, appears to be an important factor in using phototherapy to upregulate neurotrophic compounds and/or regulate neurotransmitters. Certain embodiments apply optimal power densities or energy densities to the intended target tissue, within acceptable margins of error.

As used herein, the term "neurotrophic benefits" refers to a therapeutic strategy for slowing, reversing or preventing depression and/or its symptoms by causing an upregulation of neurotrophic factors in the brain. Neurotrophic factors include those which result in or assist: (i) neurogenesis, the creation and/or growth of new neural cells; (ii) neural growth, the growth of existing neural cells and/or portions thereof, such as axons or dendrites; and (iii) plasticity of neural function, the ability to create and/or revise neural pathways in the brain and CNS for a given function or functions.

As used herein, the term "depression-effective" as used herein refers to a characteristic of an amount of light energy, wherein the amount is a power density of the light energy measured in $mW/cm^2$. A depression-effective amount of light energy achieves the goal of causing a diminishment or elimination of depression and its symptoms, and/or delays, reduces, or eliminates the onset of depression or depressive symptoms. It is believed that these effects are caused by an upregulation of endogenous compounds in the brain, including neurotrophic factors, that serve to enhance neural growth, neurogenesis, and/or plasticity of neural function;

and/or they are caused by regulation of the presence, concentration, and/or balance of neurotransmitters in the brain.

Thus, one method for the treatment of depression in a patient in need of such treatment involves delivering a depression-effective amount of light energy having a wavelength in the visible to near-infrared wavelength range to a target area of the patient's brain 20. In certain embodiments, the target area of the patient's brain 20 includes the hippocampus, believed to be instrumental in depression and its symptoms. In other embodiments, the target area includes other portions of the brain 20 not within the hippocampus. The light energy delivered preferably causes neurotrophic benefits and/or regulation of neurotransmitters. Additional information regarding the biomedical mechanisms or reactions involved in phototherapy is provided by Tiina I. Karu in "Mechanisms of Low-Power Laser Light Action on Cellular Level", Proceedings of SPIE Vol. 4159 (2000), Effects of Low-Power Light on Biological Systems V, Ed. Rachel Lubart, pp. 1-17, which is incorporated in its entirety by reference herein.

In certain embodiments, delivering the depression effective amount of light energy includes selecting a surface power density of the light energy at the scalp 30 corresponding to the predetermined power density at the target area of the brain 20. As described above, light propagating through tissue is scattered and absorbed by the tissue. Calculations of the power density to be applied to the scalp 30 so as to deliver a predetermined power density to the selected target area of the brain 20 preferably take into account the attenuation of the light energy as it propagates through the skin and other tissues, such as bone and brain tissue. Factors known to affect the attenuation of light propagating to the brain 20 from the scalp 30 include, but are not limited to, skin pigmentation, the presence and color of hair over the area to be treated, amount of fat tissue, the presence of bruised tissue, skull thickness, and the location of the target area of the brain 20, particularly the depth of the area relative to the surface of the scalp 30. For example, to obtain a desired power density of 50 mW/cm$^2$ in the brain 20 at a depth of 3 cm below the surface of the scalp 30, phototherapy may utilize an applied power density of 500 mW/cm$^2$. The higher the level of skin pigmentation, the higher the power density applied to the scalp 30 to deliver a predetermined power density of light energy to a subsurface site of the brain 20.

In certain embodiments, treating a patient comprises placing the therapy apparatus 10 in contact with the scalp 30 and adjacent a target area of the patient's brain 20. The target area of the patient's brain 20 can be previously identified such as by using standard medical imaging techniques. In certain embodiments, treatment further includes calculating a surface power density at the scalp 30 which corresponds to a preselected power density at the target area of the patient's brain 20. The calculation of certain embodiments includes factors that affect the penetration of the light energy and thus the power density at the target area. These factors include, but are not limited to, the thickness of the patient's skull, type of hair and hair coloration, skin coloration and pigmentation, patient's age, patient's gender, and the distance to the target area within or on the surface of the brain 20. The power density and other parameters of the applied light are then adjusted according to the results of the calculation.

The power density selected to be applied to the target area of the patient's brain 20 depends on a number of factors, including, but not limited to, the wavelength of the applied light, and the patient's clinical condition. The power density of light energy to be delivered to the target area of the patient's brain 20 may also be adjusted to be combined with any other therapeutic agent or agents, such as antidepressants, to achieve the desired biological effect. In such embodiments, the selected power density can also depend on the additional therapeutic agent or agents chosen.

In preferred embodiments, the treatment proceeds continuously for a period of about 10 seconds to about 2 hours, more preferably for a period of about 1 to about 10 minutes, and most preferably for a period of about 1 to 5 minutes. In other embodiments, the light energy is preferably delivered for at least one treatment period of at least about five minutes, and more preferably for at least one treatment period of at least ten minutes. The light energy can be pulsed during the treatment period or the light energy can be continuously applied during the treatment period.

In most circumstances, the treatment is repeated for several treatment periods. The time between subsequent treatment periods is preferably at least about five minutes, more preferably at least about 1 to 2 days, and but may be as long as one week or more. In certain embodiments in which treatment is performed over the course of multiple days, the apparatus 10 is wearable over multiple concurrent days (e.g., embodiments of FIGS. 1, 3, 9A, 10, and 13). The length of treatment time and frequency of treatment periods can depend on several factors, including the recovery of the patient. Because it may take one week or more to achieve outwardly noticeable neurotrophic benefits, treatment preferably proceeds over the course of several weeks. In certain embodiments, such as in patients who suffer from chronic depression or dysthmia, treatment periods may be repeated and continued for an extended period of time. In some embodiments, treatment may commence following a traumatic or stressful event or other event or situation that may trigger depression in individuals so as to counteract the influence of stress hormones that may cause depressive changes in the brain and cause an episode of depression.

During the treatment, the light energy may be continuously provided, or it may be pulsed. If the light is pulsed, the pulses are preferably at least about 10 nanosecond long and occur at a frequency of up to about 100 kHz. Continuous wave light may also be used.

In certain embodiments, the phototherapy is combined with other types of treatments for an improved therapeutic effect. Treatment can comprise directing light through the scalp of the patient to a target area of the brain concurrently with applying an electromagnetic field to the brain. In such embodiments, the light has an efficacious power density at the target area and the electromagnetic field has an efficacious field strength. For example, the apparatus 50 can also include systems for electromagnetic treatment, e.g., as described in U.S. Pat. No. 6,042,531 issued to Holcomb, which is incorporated in its entirety by reference herein. In certain embodiments, the electromagnetic field comprises a magnetic field, while in other embodiments, the electromagnetic field comprises a radio-frequency (RF) field. As another example, treatment can comprise directing an efficacious power density of light through the scalp of the patient to a target area of the brain concurrently with applying an efficacious amount of ultrasonic energy to the brain. Such a system can include systems for ultrasonic treatment, e.g., as described in U.S. Pat. No. 5,054,470 issued to Fry et al., which is incorporated in its entirety by reference herein.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A method of treating or preventing depression, the method comprising:
   non-invasively irradiating at least a portion of a patient's brain with light energy having an efficacious power density and wavelength sufficient to cause a neurotrophic effect and/or regulation of neurotransmitters, wherein the light energy has a power density of at least about 5 mW/cm$^2$ at a depth of approximately 2 centimeters below the dura.

2. The method of claim 1, wherein the treatment causes a diminishment or elimination of depression and its symptoms.

3. The method of claim 1, wherein the light energy has a wavelength between about 630 nanometers to about 1064 nanometers.

4. The method of claim 1, wherein the light energy has a wavelength between about 780 nanometers and about 840 nanometers.

5. The method of claim 1, wherein the light energy has a power density between about 100 mW/cm$^2$ and about 10 W/cm$^2$ at the surface of the scalp.

6. The method of claim 1, further comprising delivering the light energy for at least one treatment period of at least about ten minutes.

7. The method of claim 1, further comprising delivering the light energy for at least one treatment period for at least about five minutes.

8. The method of claim 7, wherein the light energy is pulsed during the treatment period.

9. The method of claim 7, wherein the light energy is continuous during the treatment period.

10. The method of claim 7, wherein the light energy is delivered in five or more treatment periods occurring over the course of at least one week.

11. A method of treating or preventing depression, the method comprising:
    irradiating at least a portion of a patient's brain with light energy having an efficacious power density and wavelength sufficient to cause a neurotrophic effect and/or regulation of neurotransmitters; and
    delivering the light energy for five or more treatment periods occurring over the course of at least one week, each treatment period having a duration of at least about five minutes.

12. The method of claim 11, wherein the light energy has a power density of at least about 0.1 mW/cm$^2$ at a depth of approximately 2 centimeters below the dura.

13. The method of claim 11, wherein the light energy has a power density of at least about 10 mW/cm$^2$ at a depth of approximately 2 centimeters below the dura.

14. The method of claim 11, wherein the light energy has a wavelength between about 630 nanometers to about 1064 nanometers.

15. The method of claim 11, wherein the light energy has a wavelength between about 780 nanometers and about 840 nanometers.

16. The method of claim 11, wherein the light energy has a power density between about 10 mW/cm$^2$ and about 10 W/cm$^2$ at the surface of the scalp.

17. The method of claim 11, wherein the light energy is pulsed during the treatment period.

18. The method of claim 11, wherein the light energy is continuous during the treatment period.

* * * * *

UNITED STATES PATENT AND TRADEMARK OFFICE
CERTIFICATE OF CORRECTION

| | | |
|---|---|---|
| PATENT NO. | : 7,309,348 B2 | Page 1 of 1 |
| APPLICATION NO. | : 11/038770 | |
| DATED | : December 18, 2007 | |
| INVENTOR(S) | : Streeter et al. | |

It is certified that error appears in the above-identified patent and that said Letters Patent is hereby corrected as shown below:

On the Title Page Item -56- at page 3, (Other Publications), line 26, delete "ot1.berkeley.edu" and insert -- otl.berkeley.edu --, therefor.

On the Title Page Item -56- at page 3, (Other Publications), line 30, delete "ischaemic" and insert -- ischemic --, therefor.

On the Title Page Item -56- at page 3, (Other Publications), line 36, delete "Michondrial" and insert -- Mitochondrial --, therefor.

On the Title Page Item -56- at page 3, (Other Publications), line 10, delete "laser-therapy" and insert -- lasertherapy --, therefor.

On the Title Page Item -56- at page 3, (Other Publications), line 17, delete "Geme" and insert -- Gene --, therefor.

On the Title Page Item -56- at page 4, (Other Publications), line 2, delete "Laster Irradation ar eMore" and insert -- Laser Irradiation are More --, therefor.

On the Title Page Item -56- at page 4, (Other Publications), line 3, delete "Biomoducation" and insert -- Biomodulation --, therefor.

At column 1, line 38, delete "Dysthmia." and insert -- Dysthymia. --, therefor.

At column 18, line 29, delete "dysthmia," and insert -- dysthymia, --, therefor.

Signed and Sealed this

Eighth Day of July, 2008

JON W. DUDAS
*Director of the United States Patent and Trademark Office*